US011351263B2

United States Patent
Gong et al.

(10) Patent No.: US 11,351,263 B2
(45) Date of Patent: Jun. 7, 2022

(54) POLYPLEX DELIVERY SYSTEM FOR PROTEINS, NUCLEIC ACIDS AND PROTEIN/NUCLEIC ACID COMPLEXES

(71) Applicant: Wisconsin Alumni Research Foundation, Madison, WI (US)

(72) Inventors: Shaoqin Gong, Middleton, WI (US); Yuyuan Wang, Madison, WI (US); Krishanu Saha, Middleton, WI (US); Amr Ashraf Abdeen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 360 days.

(21) Appl. No.: 16/282,174

(22) Filed: Feb. 21, 2019

(65) Prior Publication Data
US 2019/0307888 A1 Oct. 10, 2019

Related U.S. Application Data

(60) Provisional application No. 62/634,156, filed on Feb. 22, 2018.

(51) Int. Cl.
*A61K 9/00* (2006.01)
*A61K 47/59* (2017.01)
(Continued)

(52) U.S. Cl.
CPC ........ *A61K 47/595* (2017.08); *A61K 31/7105* (2013.01); *A61K 38/465* (2013.01);
(Continued)

(58) Field of Classification Search
CPC .................................................. A61K 47/595
See application file for complete search history.

(56) References Cited

U.S. PATENT DOCUMENTS 5,661,025 A 8/1997 Szoka et al.
2013/0332133 A1 12/2013 Horn et al.

FOREIGN PATENT DOCUMENTS

WO WO-2015/089419 A2 6/2015

OTHER PUBLICATIONS

Bai, et al., "Simultaneous detection and quantification of mitochondrial DNA deletion(s), depletion, and over-replication in patients with mitochondrial disease," The Journal of Molecular Diagnostics, Nov. 2005, vol. 7, Issue 5, pp. 613-622.
(Continued)

*Primary Examiner* — Paul W Dickinson
(74) *Attorney, Agent, or Firm* — Foley & Lardner LLP

(57) ABSTRACT

Provided herein are nanoplexes comprising a payload selected from a protein and/or a polynucleic acid; and a plurality of copolymers comprising a first copolymer that is poly(N,N'-bis(acryloyl)cystamine-poly(aminoalkyl)) (PBAP), a second copolymer that is poly($C_{2-3}$ akylene glycol)-PBAP-poly($C_{2-3}$ akylene glycol), and a third copolymer that is TG-poly($C_{2-3}$ akylene glycol)-PBAP-poly($C_{2-3}$ akylene glycol)-TG wherein TG at each occurrence is independently a targeting ligand, a cell penetrating peptide, an imaging agent or a capping group, provided that a plurality of TG groups is a targeting ligand; wherein the payload is non-covalently complexed to one or more of the copolymers, one or more of the first, second, and/or third copolymers comprises an endosomal escape group having a pKa of about 4.5 to about 6.5, and optionally one or more of the first, second, and/or third copolymers comprises a host and a guest non-covalent crosslinker.

32 Claims, 19 Drawing Sheets

Specification includes a Sequence Listing.

(51) Int. Cl.
  A61K 47/61    (2017.01)
  A61K 31/7105  (2006.01)
  A61K 51/06    (2006.01)
  A61K 38/46    (2006.01)
  A61K 49/00    (2006.01)

(52) U.S. Cl.
  CPC .......... *A61K 47/61* (2017.08); *A61K 49/0054* (2013.01); *A61K 51/065* (2013.01)

(56) References Cited

OTHER PUBLICATIONS

Cardenas, et al., "Selective Vulnerability of Cancer Cells by Inhibition of CA (2) Transfer from Endoplasmic Reticulum to Mitochondria," Cell Reports, Mar. 2016, pp. 2313-2324, vol. 14, Issue 10.
Christofk, et al., "The M2 splice isoform of pyruvate kinase is important for cancer metabolism and tumour growth," Nature, Mar. 2008, pp. 230-233, vol. 452.
Clayton, et al., "Isolation of mitochondria from tissue culture cells," Cold Spring Harbor Protocols, 2014, pp. 1109-1112.
Ho, et al., "Phosphoenolpyruvate is a Metabolic Checkpoint of Anti-tumor T Cell Responses," Cell, Sep. 2015, vol. 162, Issue 6, pp. 1217-1228.
Lunt, et al., "Pyruvate kinase isoform expression alters nucleotide synthesis to impact cell proliferation," Molecular Cell, Jan. 2015, vol. 57, Issue 1, pp. 95-107.
Minn, et al., "Genes that mediate breast cancer metastasis to lung," Nature, Jul. 2005, vol. 436, pp. 518-524.
Sanchez, et al., "Genome-wide analysis of the human p53 transcriptional network unveils a lucRNA tumour suppressor signature," Nature Communications, 2014, vol. 5, pp. 1-13.
Wang, et al., "CARM1 methylates chromatin remodeling factor BAF155 to enhance tumore progression and metastasis," Cancer Cell, Jan. 2014, vol. 25, Issue 1, pp. 21-26.
Arnold et al., Engineered polymeric nanoparticles to guide the cellular internalization and trafficking of small interfering ribonucleic acids, Journal of Controlled Release, vol. 259, Feb. 21, 2017, URL: http://www.sipcd.com/upload/1503907118588304.pdf, pp. 3-15.
Arvizo, R. et al., Effect of Nanoparticle Surface Charge at the Plasma Membreane and Beyond, Nano letters 2010, 10, 2543-2548.
Brumbach et al., Mixtures of poly(triethylenetetramine/cystamine bisacrylamide) and poly (triethylenetetramine/cystamine bisacrylamide)-g-polyethylene glycol for improved gene delivery, Bioconjugate Chemistry, vol. 21, No. 10, Oct. 20, 2011, URL: https://www.ncbi.nlm.nih.gov/pmc/articles/PMC2958694/pdf/nihms241669.pdf, entire document.
Carlson-Stevermer, J. et al., Assembly of CRISPR ribonucleoproteins with biotinylated oligonucleotides via an RNA aptamer for precise gene editing, Nature Communications 2017, 8, 1711.
Chen et al., A Universal GSH-Responsive Nanoplatform for the Delivery of DNA, mRNA, and Cas9/sgRNA Ribonucleoprotein, ACS Applied Materials & Interfaces, vol. 10, No. 22, Sep. 17, 2018, URL: https://www.ncbi.nlm.nih.gov/pmc/articles/PMC6141193/pdf/nihms-986704.pdf. pp. 1-19.
E. Frohlich, The role of surface charge in cellular uptake and cytotoxicity of medical nanoparticles, International Journal of Nanomedicine 2012, 7, 5577-5591.
International Search Report and Written Opinion in PCT/US2016/019051 dated Apr. 29, 2019 (10 pages).
Karvelis et al., Current Opinion in Microbiology 2017, 37:88-94.
Komor, A.C. et al. CRISPR-based Technologies for the Manipulation of Eukaryotic Genomes, Cell 168:20-36 (2017).
Lee, Y., et al., Charge-Conversion Ternary Polyplex with Endosome Disruption Moiety: A Technique for Efficient and Safe Gene Delivery, Angewandte Chemie 2008, 120, 5241-5244.
Moret, I, et al., Journal of Controlled Release 2001, 76, 169-181.
Murovec, J. et al., New variants of CRISPR RNA-guided genome editing enzymes, Plant Biotechnol. J. 15:917-26 (2017).
Oba, M., et al., N. Nishiyama, Polyplex micelles prepared from u-cholesteryl PEG-polycation block copolymers for systemic gene delivery, Biomaterials 2011, 32, 652-663.
Polysciences, Inc., N,N'-Cystaminebisacrylamide, Electro Pure™, Oct. 24, 2017, URL: https://web.archive.org/web/20171024092907/http://www.polysciences.com/default/nn-cystaminebisacrylamide-electro-pure.
Sarett, S, et al., Journal of Controlled Release 218 (2015), 94-113.
Wang et al., Versatile Redox-Responsive Polyplexes for the Delivery of Plasmid DNA, Messenger RNA, and CRISPR-Cas9 Genome-Editing Machinery, ACS Applied Materials & Interfaces, 2018, 10, 31915-31927.
Wang et al., Versatile Redox-Responsive Polyplexes for the Delivery of Plasmid DNA, Messenger RNA, and CRISPR-Cas9 Genome-Editing Machinery, ACS Applied Materials & Interfaces, vol. 10, No. 38, Sep. 17, 2018, URL: https://pubs.acs.org/doi/abs/10.1021/acsami.8b09642, abstract.
Wang, R.E., et al., A homogeneous fluorescent sensor for human serum albumin, Journal of Pharmaceutical and Biomedical Analysis 2012, 63, 165-169.
Byrom, et al., "Inducing RNAi with siRNA Cocktails Generated by RNase III," AmbionTechNotes, 2003, vol. 10, No. 1, pp. 4-6.
Calegari, et al., "Tissue-specific RNA interference in postimplantation mouse embryos with endoribonuclease-prepared short interfering RNA," PNAS, Oct. 29, 2002, vol. 99, No. 22, pp. 14236-14240.
Final Office Action in U.S. Appl. No. 15/819,424 dated Dec. 23, 2019 (11 pages).
Guidry, et al., "Improving the in vivo therapeutic index of siRNA polymer conjugates through increasing pH responsiveness," Bioconjugate Chem., 2014, vol. 25, pp. 296-307.
Han, et al., "Transfection study using multicellular tumor spheroids for screening non-viral polymeric gene vectors with low cytotoxicity and high transfection efficiencies," J. Controlled Release, 2007, vol. 121, pp. 38-48.
Heise, et al., "Starlike block copolymers with amphiphilic arms as models for unimolecular micelles," J. Am. Chem. Soc. 1999, vol. 121, pp. 8647-8648.
Kawasaki, et al., "siRNAs generated by recombinant human Dicer induce specific and significant but target site-independent gene silencing in human cells," Nucleic Acids Research, Feb. 1, 2003, vol. 31, Issue 3, pp. 981-987.
Kesharwani, eT al., "PAMAM dendrimers as promising nanocarriers for RNAi therapeutics," Mat. Today, 2015, vol. 18, pp. 565-572.
Kim, et al., "Overcoming the barriers in micellar drug delivery: loading efficiency, in vivo stability, and micelle-cell interaction," Expert Opin. Drug Deliv., 2010, vol. 7, pp. 49-62.
Knight, et al., "A Role for the RNase III Enzyme DCR-1 in RNA Interference and Germ Line Development in Caenorhabditis elegans," Science, Sep. 21, 2001, vol. 293, Issue 5538, pp. 2269-2271.
M.J. Lawrence, "Surfactant systems: their use in drug delivery," Chem. Soc. Rev., 1994, vol. 23, pp. 417-424.
Maeda, et al., Analyses of repeated failures in cancer therapy for solid tumors: poor tumor-selective drug delivery, low therapeutic efficacy and unsustainable costs,: Clin. Transl. Med., 2011, vol. 7, Issue 11, pp. 1-20.
Meyer, et al., "Synthesis and biological evaluation of a bioresponsive and endosomolytic siRNA-polymer conjugate," Mol. Pharm., 2009, vol. 6, pp. 752-762.
Moller, et al., "Highly Efficient siRNA Delivery from Core-Shell Mesoporous Silica Nanoparticles with Multifunctional Polymer Caps," Nanoscale, 2016, vol. 8, pp. 4007-4019.
Non-Final Office Action in U.S. Appl. No. 15/819,424 dated Aug. 12, 2020.
Non-Final Office Action in U.S. Appl. No. 15/819,424 dated Jun. 12, 2019 (17 pages).
Non-Final Office Action in U.S. Appl. No. 15/892,140 dated Jul. 1, 2019 (10 pages).
Notice of Allowance in U.S. Appl. No. 15/892,140 dated Jan. 13, 2020 (9 pages).

(56) References Cited

OTHER PUBLICATIONS

Patil, et al., "Multifunctional Triblock Nanocarrier (PAMAM-PEG-PLL) for the Efficient Intracellular siRNA Delivery and Gene Silencing," ACSNANO, 2011, vol. 5, No. 3, pp. 1877-1887.

Prabaharan, et al., "Amphiphilic Multi-Arm-Block Copolymer Conjugated with Doxorubicin Via pH-Sensitive Hydrazone Bond for Tumor-Targeted Drug Delivery," Biomaterials, Oct. 2009, pp. 5757-5766, vol. 30, Issue 29.

Robertson, et al., "Purification and Properties of Ribonuclease III from *Escherichia coli*," Journal of Biological Chemistry, Jan. 10, 1968, vol. 243, No. 1, pp. 82-91.

Segovia, et al., "Hydrogel doped with nanoparticles for local sustained release of siRNA in breast cancer," Advanced Healthcare Materials, Jan. 28, 2015, vol. 4, Issue 2, pp. 271-280.

Sun, et al., "The blood clearance kinetics and pathway of polymeric micelles in cancer drug delivery," ACS Nano, 2018, vol. 12, pp. 6179-6192.

Takeda, et al., "Effect of shear stress on structure and function of polyplex micelles from poly (ethylene glycol)-poly (L-lysine) block copolymers as systemic gene delivery carrier," Biomaterials, 2017, vol. 126, pp. 31-38.

Wang, et al., "Enhancing the In Vitro and In Vivo Stabilities of Polymeric Nucleic Acid Delivery Nanosystems," Bioconjugate Chemistry, 2018, vol. 30, No. 2, pp. 325-337.

Yang, et al., "Short RNA duplexes produced by hydrolysis with *Escherichia coli* RNase III mediate effective RNA interference in mammalian cells," PNAS, Jul. 23, 2002, pp. 9942-9947, vol. 99, No. 15.

Yu, et al., "Polyactide-graft-doxorubicin nanoparticles with precisely controlled drug loading for pH-triggered drug delivery," Biomacromolecules, 2014, vol. 15, pp. 524-532.

CLPBAP polymers: PBAP-based polymers used to form crosslinked polyplexes

CLPBAP copolymers: p(BAC-TET-Im/AD) (top)
p(BAC-TET-Im/β-CD) (bottom)

PEG-CLPBAP-PEG copolymer: PEG-p(BAC-TET-Im/AD)-PEG

PBAPpolymers: PBAP-based polymers used to form non-crosslinked polyplexes

PBAP polymer: p(BAC-TET-Im)

PEG-PBAP-PEG copolymer: PEG-p(BAC-TET-Im)-PEG

US 11,351,263 B2

POLYPLEX DELIVERY SYSTEM FOR PROTEINS, NUCLEIC ACIDS AND PROTEIN/NUCLEIC ACID COMPLEXES

CROSS-REFERENCE TO RELATED APPLICATIONS

This application claims the benefit of and priority to U.S. Provisional Patent Application No. 62/634,156, filed on Feb. 22, 2018, the entire contents of which are incorporated herein by reference.

SEQUENCE LISTING

The instant application contains a Sequence Listing which has been filed electronically in ASCII format and is hereby incorporated by reference in its entirety. Said ASCII copy, created on Jun. 18, 2019, is named 032026-1393_SL.txt and is 12,637 bytes in size.

STATEMENT OF GOVERNMENT SUPPORT

This invention was made with government support under GM119644 and CA166178 awarded by the National Institutes of Health. The government has certain rights in the invention.

FIELD

The present technology relates generally to the field of nanoplatform delivery systems. The delivery systems include a polyplex of payload biomacromolecules and cationic copolymers. The polymers are redox-responsive copolymers containing disulfide bonds which can deliver proteins, nucleic acids and complexes of proteins and nucleic acids to cells.

BACKGROUND

Gene therapy has demonstrated tremendous therapeutic potential to prevent and treat a wide range of pathological conditions over the last two decades. However, clinical translation has been limited due to various technical barriers, particularly, the lack of safe and efficient gene delivery systems.

Both plasmid DNA (DNA) and messenger RNA (mRNA) have been widely investigated for gene therapy. Both DNA and mRNA can be used to express functional proteins. To function, mRNA needs to reach the cytosol of the target cell, while DNA usually translocates to the cell nucleus for transgene expression. Both DNA and mRNA can result in relatively safe and rapid protein production for disease treatment. However, due to their relatively large sizes and high negative charge densities, naked DNA and mRNA exhibit low cellular uptake efficiency. Furthermore, naked DNA and mRNA are also susceptible to chemical degradation.

The clustered regularly interspaced short palindromic repeats (CRISPR)-Cas9 systems are powerful tools for genome editing. The Cas9/sgRNA ribonucleoprotein (RNP) can knock-out a target gene with high efficiency and specificity. Moreover, the combination of RNP and single-stranded donor oligonucleotide (ssODN) used as the repair template (i.e., RNP-ssODN, for example, a recently reported S1mplex) can achieve precise genome editing to incorporate sequences from the ssODN. However, safe and efficient delivery of RNP and S1mplex remains as a significant challenge for their potential application owing to their relatively large and complex structures. Similar to DNA and mRNA, unpackaged RNP and S1mplex are also susceptible to chemical degradation. Furthermore, in comparison to DNA and mRNA delivery, the delivery of protein/nucleic acid complexes such as RNP and S1mplex is even more challenging due to the mixed charges (e.g., positively charged Cas9 protein and negatively charged sgRNA and ssODN) and more sophisticated structures.

SUMMARY OF THE INVENTION

The present technology provides compositions utilizing cationic polymer-based nanovectors and methods for achieving high transfection or genome editing efficiencies with polynucleic acids (e.g., DNA and mRNA) and protein-nucleic acid complexes (e.g., CRISPR-Cas9 genome editing machinery). The present compositions not only protect genetic materials from degradation, but also show improved stability in vivo. They are readily taken up by target cells and rapidly release the intact genetic materials to the desired subcellular space (e.g., nucleus for DNA, Cas9 RNP, and S1mplex; cytosol for mRNA) of the target cells. Unlike many current non-viral vectors, the present compositions also exhibit low cytotoxicity. Due to their chemical versatility, high reproducibility, low cytotoxicity, and low cost, the present compositions and methods provide superior performance over previous non-viral vectors.

Thus, in one aspect, these polyplex are formed by mixing a negatively charged payload such as a polynucleic acid, a protein and a protein/nucleic acid complex and a plurality of redox-responsive cationic copolymers. The latter are made up of at least one type of copolymer: a first copolymer that is poly(N,N'-bis(acryloyl)cystamine-poly(aminoalkyl)) (PBAP), Additional types of copolymers may be used in the polyplex: e.g., optionally a second copolymer that is poly($C_{2-3}$ akylene glycol)-PBAP-poly($C_{2-3}$ akylene glycol) may be used, and/or a third copolymer may be used: TG-poly($C_{2-3}$ akylene glycol)-PBAP-($C_{2-3}$ akylene glycol)-TG wherein TG at each occurrence is independently a targeting ligand, a cell penetrating peptide, an imaging agent or a capping group, provided that a plurality of TG groups is a targeting ligand. The payload may be non-covalently complexed to one or more of the cationic polymers, e.g., by electrostatic interactions between negatively charged groups on the protein and/or polynucleic acid and the positively charged copolymer backbone and side chains. One or more of the first, second, and/or third copolymers includes an endosomal escape group having a pKa of about 4.5 to about 6.5. Optionally, one or more of the first, second, and/or third copolymers comprises non-covalent crosslinkers based on host-guest interactions. The present technology also includes methods of delivering a payload to a targeted cell. The methods include exposing a target cell to a polyplex delivery system as described herein. The methods include administering the polyplex delivery system as described herein to a subject in need thereof.

While not wishing to be bound by theory, it is believed that the noncovalent bonding between the charged interior of the polyplex and the payload, whether a protein, nucleic acid or complex between them, protects the payload from degradation in the extracellular environment and assists in delivery of the payload into cells as shown in the illustrative embodiment of FIG. 1. The size of the polyplexes (e.g., having a hydrodynamic diameter of about 130-200 nm) as well as any targeting ligand present allow the polyplexes to enter the target cells by endocytosis. The presence of the imidazole groups in the copolymers facilitate endosomal escape of the polyplexes, because imidazole groups, having a pKa value of ~6.0, can be protonated in the acidic endosomes. This absorption of protons leads to endosomal-membrane disruption, thereby enabling release of the polyplexes into the cytosol. There, due to the glutathione (GSH)-rich environment of the cytosol (2-10 mM), the disulfide bonds present in the main chain of the redox-responsive cationic polymers are reduced, causing the breakdown of the cationic polymers and the disassembly of the polyplexes, thereby releasing the payload. Once released from the polyplex, the payload is available to perform its function in the cell. For example, RNPs can enter the nucleus, optionally facilitated by one or more nuclear localization signals (NLSs), on Cas9 proteins, and perform its gene editing functions.

BRIEF DESCRIPTION OF THE DRAWINGS

(FIG. 1A) Illustrative embodiment of a crosslinked PBAP polyplex (CLPBAP) for various genetic materials delivery. (FIG. 1B) Chemical structures of an illustrative embodiment of PBAP-based polymers used to form crosslinked polyplexes including the CLPBAP polymers (i.e., p(BAC-TET-Im/AD), p(BAC-TET-Im/β-CD)), and PEG-p(BAC-TET-Im/AD)-PEG. TET: Triethylenetetramine; BAC: N,N'-bis(acryloyl) cystamine; PEG: A poly(ethylene glycol); Im: imidazole. (FIG. 1C) Chemical structures of an illustrative embodiment of PBAP-based polymers used to prepare non-crosslinked PBAP polyplexes including the PBAP polymers p(BAC-TET-Im) and PEG-p(BAC-TET-Im)-PEG.

(FIG. 7A) The effects of polyplex formulation on the DNA transfection efficiency of polyplexes. Cells were treated with Lipofectamine™ 2000 (Lipo 2000), non-crosslinked polyplexes with three different PBAP:PEG-PBAP-PEG:DNA weight ratios, as well as the polyplex with a PBAP:PEG-PBAP-PEG:DNA weight ratio of 48:28:1 together with NLS (N/P ratio=0.25). (FIG. 7B) Effects of polyplex formulation on the cytotoxicity of non-crosslinked DNA polyplexes with different weight ratios. NS: not significant, *: $p<0.05$; **: $p<0.01$; n=3.

(FIG. 10A) Transfection efficiency of PEG- or imidazole-lacking crosslinked DNA polyplexes. (FIG. 10B) Cell viability of PEG-lacking crosslinked DNA polyplexes. NS: not significant, *: $p<0.05$; *: $p<0.001$; **: $p<0.0001$; n=3.

(FIGS. 12B-C) Transfection efficiency of the non-crosslinked and crosslinked mRNA polyplexes in (B) HEK 293 cells and (C) RAW 264.7 cells at various time points. The weight ratios of PBAP:PEG-PBAP-PEG:mRNA or CLPBAP:PEG-CLPBAP-PEG:mRNA in the PBAP and CLPBAP polyplexes, respectively, were fixed at 48:24:1. *: $p<0.05$; **: $p<0.01$; n=3.

DETAILED DESCRIPTION

Figure 1A:
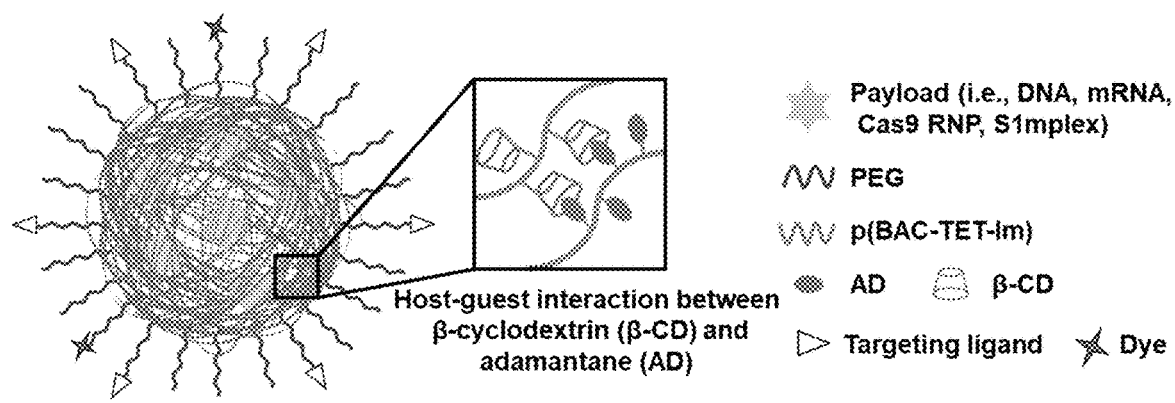
FIGS. 1A-1C show schematic representations of an illustrative embodiment of the present technology.
Figure 1B:
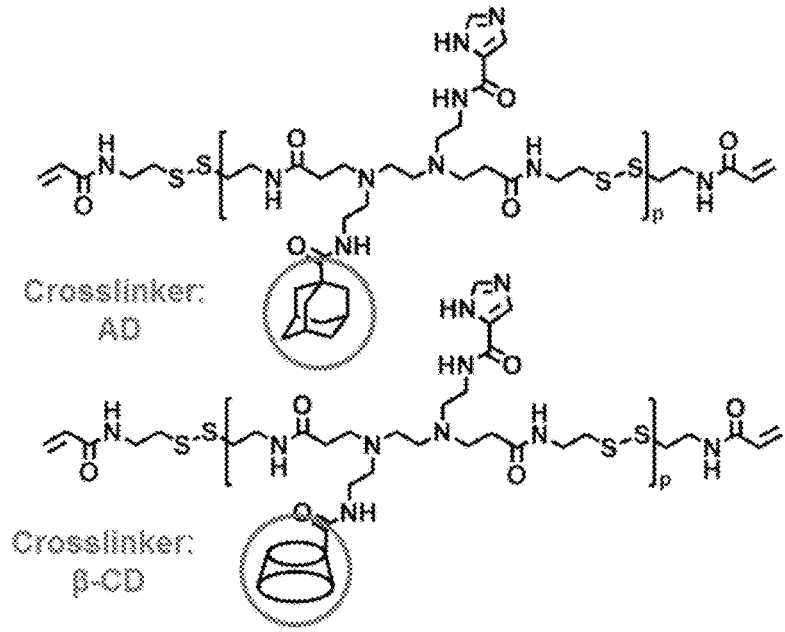
Figure 1B:
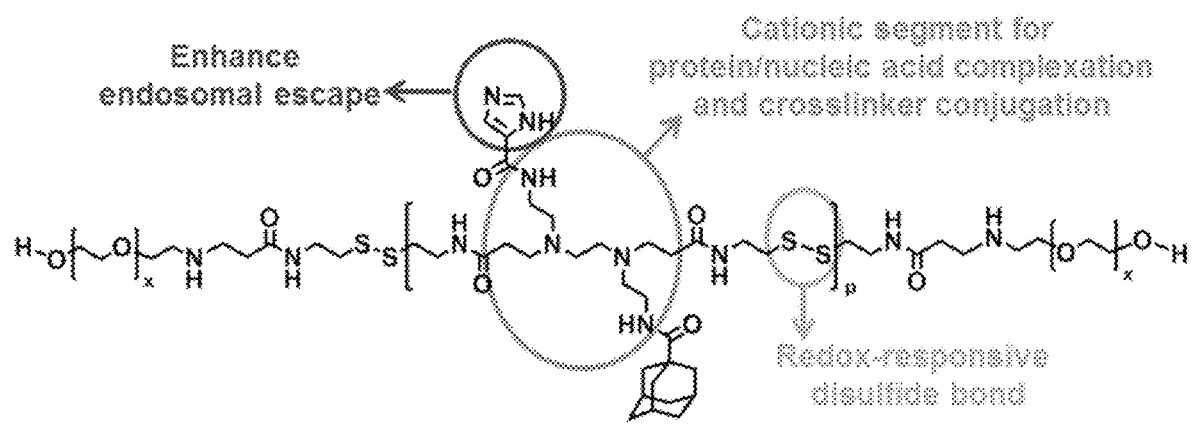

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York). Amino protecting groups include, but are not limited to, mesitylenesulfonyl (Mts), benzyloxycarbonyl (Cbz or Z), t-butyloxycarbonyl (Boc), t-butyldimethylsilyl (TBS or TBDMS), 9-fluorenylmethyloxycarbonyl (Fmoc), allyloxycarbonyl (Alloc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α,α-dimethyldimethoxybenzyloxycarbonyl (DDZ), 5-bromo-7-nitroindolinyl, and the like. Amino protecting groups susceptible to acid-mediated removal include but are not limited to Boc and TBDMS. Amino protecting groups resistant to acid-mediated removal and susceptible to hydrogen-mediated removal include but are not limited to Alloc, Cbz, nitro, and 2-chlorobenzyloxycarbonyl.

As used herein, "Cas9 polypeptide" (also known as "Cas9") refers to Cas9 proteins and variants thereof having nuclease activity, as well as fusion proteins containing such Cas9 proteins and variants thereof. The fused proteins may include those that modify the epigenome or control transcriptional activity. The variants may include deletions or additions, such as, e.g., addition of one, two, or more nuclear localization sequences (such as from SV40 and others known in the art), e.g., 1, 2, 3, 4, 5, 6, 7, 8, 9, 10 such sequences or a range between and including any two of the foregoing values. In some embodiments the Cas9 polypeptide is a Cas9 protein found in a type II CRISPR-associated system. Suitable Cas9 polypeptides that may be used in the present technology include, but are not limited to Cas9 protein from *Streptococcus pyogenes* (Sp.Cas9), *F. novicida, S. aureus, S. thermophiles, N. meningitidis*, and variants thereof. In some embodiments, the Cas9 polypeptide is a wild-type Cas9, a nickase, or comprises a nuclease inactivated (dCas9) protein. In some embodiments, the Cas9 polypeptide is a fusion protein comprising dCas9. In some embodiments, the fusion protein comprises a transcriptional activator (e.g., VP64), a transcriptional repressor (e.g., KRAB, SID) a nuclease domain (e.g., FokI), base editor (e.g., adenine base editors, ABE), a recombinase domain (e.g., Hin, Gin, or Tn3), a deaminase (e.g., a cytidine deaminase or an adenosine deaminase) or an epigenetic modifier domain (e.g., TET1, p300). In some embodiments, the Cas9 polypeptide includes variants with at least 85% sequence identity, at least 90% sequence identity, at least 95% sequence identity, or even 96%, 97%, 98%, or 99% sequence identity to the wild type Cas9. Accordingly, a wide variety of Cas9 polypeptides may be used as formation of the polyplex is not sequence dependent so long as the the Cas9 polypeptide can complex with nucleic acids and the resulting RNP has sufficient negatively charged residuals to allow complexation with the cationic redox-responsive PBAP-based polymers of the present technology. Other suitable Cas9 polypeptides may be found in Karvelis, G. et al. "Harnessing the natural diversity and in vitro evolution of Cas9 to expand the genome editing toolbox," *Current Opinion in Microbiology* 37: 88-94 (2017); Komor, A. C. et al. "CRISPR-Based Technologies for the Manipulation of Eukaryotic Genomes," *Cell* 168:20-36 (2017); and Murovec, J. et al. "New variants of CRISPR RNA-guided genome editing enzymes," *Plant Biotechnol. J.* 15:917-26 (2017), each of which is incorporated by reference herein in their entirety.

As used herein, "cyclodextrin" refers to cyclic rings of 5 to 8 α-D-glucopyranosides (such as glucose) linked by α-1,4-glycosidic bonds. The rings form a cone-shape structure that is typically more hydrophobic on the interior than on the exterior. The interior thus may non-covalently interact with other molecules, especially more hydrophobic ones with appropriate sizes such as adamantane or azobenzene, by host-guest interaction. By "host-guest interaction" is meant a specific non-covalent binding between two molecular entities.

"Molecular weight" as used herein with respect to polymers refers to number-average molecular weights ($M_n$) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and N,N'-dimethylformamide (DMF) as the eluent. "Molecular weight" in reference to small molecules and not polymers is actual molecular weight, not number-average molecular weight.

The phrase "targeting ligand" refers to a ligand that binds to "a targeted receptor" that distinguishes the cell being targeted from other cells. The ligands may be capable of binding due to expression or preferential expression of a receptor for the ligand, accessible for ligand binding, on the target cells. Examples of such ligands include GE11 peptide, anti-EGFR nanobody, cRGD ((cyclo (RGDfC)), KE108 peptide, octreotide, glucose, folic acid, prostate-specific membrane antigen (PSMA) aptamer, TRC105, a human/murine chimeric IgG1 monoclonal antibody, mannose, and cholera toxin B (CTB). Additional examples of such ligands include Rituximab, Trastuzumab, Bevacizumab, Alemtuzumab, Panitumumab, RGD, DARPins, RNA aptamers, DNA aptamers, analogs of folic acid and other folate receptor-binding molecules, lectins, other vitamins, peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, microtubule-associated sequence (MTAS), various galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of targeted cells or on an infectious organism, or fragments of any of these molecules.

The phrase "a targeted receptor" refers to a receptor expressed by a cell that is capable of binding a cell targeting ligand. The receptor may be expressed on the surface of the cell. The receptor may be a transmembrane receptor. Examples of such targeted receptors include EGFR, $\alpha_v\beta_3$ integrin, somatostatin receptor, folate receptor, prostate-specific membrane antigen, CD105, mannose receptor, estrogen receptor, and GM1 ganglioside.

In some embodiments, cell penetrating peptides may also be attached to one or more PEG terminal groups in place of or in addition to the targeting ligand. A "cell penetrating peptide" (CPP), also referred to as a "protein transduction domain" (PTD), a "membrane translocating sequence," and a "Trojan peptide", refers to a short peptide (e.g., from 4 to about 40 amino acids) that has the ability to translocate across a cellular membrane to gain access to the interior of a cell and to carry into the cells a variety of covalently and noncovalently conjugated cargoes, including proteins, oligonucleotides, and liposomes. They are typically highly cationic and rich in arginine and lysine amino acids. Examples of such peptides include TAT cell penetrating peptide (GRKKRRQRRRPQ); MAP (KLALKLALKAL-KAALKLA); Penetratin or Antenapedia PTD (RQIKWFQNRRMKWKK); Penetratin-Arg: (RQIRIWFQNRRMRWRR); antitrypsin (358-374): (CSIPPEVKFNKPFVYLI); Temporin L: (FVQWFSKFL-GRIL-NH2); Maurocalcine: GDC(acm) (LPHLKLC); pVEC (Cadherin-5): (LLIILRRRIRKQAHAHSK); Calcitonin: (LGTYTQDFNKFHTFPQTAIGVGAP); Neurturin: (GAAEAAARVYDLGLRRLRQRRRLRRERVRA); Penetratin: (RQIKIWFQNRRMKWKKGG); TAT-HA2 Fusion Peptide: (RRRQRRKKRGGDIMGEWGNEIFGA-IAGFLG); TAT (47-57) Y(GRKKRRQRRR); SynB 1 (RG-GRLSYSRRRFSTSTGR); SynB3 (RRLSYSRRRF); PTD-4 (PIRRRKKLRRL); PTD-5 (RRQRRTSKLMKR); FHV Coat-(35-49) (RRRRNRTRRNRRRVR); BMV Gag-(7-25) (KMTRAQRRAAARRNRWTAR); HTLV-II Rex-(4-16) (TRRQRTRRARRNR); HIV-1 Tat (48-60) or D-Tat (GRKKRRQRRRPPQ); R9-Tat (GRRRRRRRRRPPQ); Transportan (GWTLNSAGYLLGKINLKALAALAKKIL chimera); SBP or Human P1 (MGLGLHLLV-LAAALQGAWSQPKKKRKV); FBP (GALFLGWL-GAAGSTMGAWSQPKKKRKV); MPG (ac-GALFLGFL-GAAGSTMGAWSQPKKKRKV-cya (wherein cya is cysteamine)); MPG(ΔNLS) (ac-GALFLGFL-GAAGSTMGAWSQPKSKRKV-cya); Pep-1 or Pep-1-Cysteamine (ac-KETWWETWWTEWSQPKKKRKV-cya); Pep-2 (ac-KETWFETWFTEWSQPKKKRKV-cya); Periodic sequences, Polyarginines (RxN (4<N<17) chimera); Polylysines (KxN (4<N<17) chimera); (RAca)6R; (RAbu) 6R; (RG)6R; (RM)6R; (RT)6R; (RS)6R; R10; (RA)6R; and R7.

A "dye" refers to small organic molecules having a molecular weight (actual, not number average) of 2,000 Da or less or a protein which is able to emit light. Non-limiting examples of dyes include fluorophores, chemiluminescent or phosphorescent entities. For example, dyes useful in the present technology include but are not limited to cyanine dyes (e.g., Cy2, Cy3, Cy5, Cy5.5, Cy7, and sulfonated versions thereof), fluorescein isothiocyanate (FITC), ALEXA FLUOR® dyes (e.g., ALEXA FLUOR® 488, 546, or 633), DYLIGHT® dyes (e.g., DYLIGHT® 350, 405, 488, 550, 594, 633, 650, 680, 755, or 800) or fluorescent proteins such as GFP (Green Fluorescent Protein).

The present technology provides polyplex delivery systems that include a payload, i.e., a biomacromolecule to be delivered to a cell, and a plurality of copolymers. The cationic copolymers interact with negatively charged payload to form polyplexes, and the copolymers within the polyplexes may be non-covalently crosslinked to each other through crosslinkers. The payload may be any suitable protein and/or polynucleic acid non-covalently complexed to one or more of the cationic copolymers, e.g., by electrostatic interactions between charged groups on the protein and/or polynucleic acid and the charged copolymer backbone and side chains. Thus, in contrast to unimolecular nanoparticles which have only been used to deliver small molecule therapeutics and siRNA, the present polyplexes are capable of delivering to a target cell both smaller therapeutics (e.g., siRNA, microRNA, and peptides etc.) and much larger biomacromolecules (e.g., up to 100 times or more of the molecular weight of a 20-25 bp siRNA). Furthermore, in contrast to nanoencapsulated Cas9 RNP which carries only a single Cas9 RNP complex per nanoparticle, the present polyplexes are able to deliver multiple molecules of the payload per polyplex, whether small or large. While the size of the present complexes are not invariant, they mostly fall within the range of 130-200 nm. The cross-linked polyplexes tend toward the higher end of this range and the non-crosslinked polyplexes tend toward the lower end.

Suitable payloads for the present polyplex delivery systems include proteins, polynucleic acids and complexes of the two such as ribonucleoproteins (RNP), e.g., Cas9 with guide RNA. Such biomacromolecules have charged groups that may undergo electrostatic interactions with the copolymers of the present polyplexes. While the biomacromolecules may have both negatively charged and positively charged groups, in some embodiments the payload has a net negative charge. By "net negative charge" is meant that the payload molecules have at least one more negative charge provided by charged groups on/in the payload than positive charges provided by charged groups on/in the payload. In some embodiments, the payload may be selected from the group consisting of pDNA, ssODN, cDNA, mRNA, siRNA, miRNA, shRNA, sgRNA, tRNA and ribozymes. In certain embodiments, the payload may be selected from the group consisting of Cas9 RNP, S1mplex (i.e., RNP-ssODN where ssODN serves as a repair template), and other Cas9-based protein/nucleic acid complexes. NLS peptides may be used to direct payload to the nucleus if desired. For example, positively charged NLS peptides may be mixed with polynucleic acids prior to polyplex formation. Alternatively, polynucleic acids as described herein as well as proteins such as Cas9 or complexes such as S1mplexes may be covalently tagged with NLS peptides.

The copolymers of the polyplex include a first copolymer that is poly(N,N'-bis(acryloyl)cystamine-poly(aminoalkyl)) (PBAP), optionally a second copolymer that is poly($C_{2-3}$ akylene glycol)-PBAP-poly($C_{2-3}$ akylene glycol), and optionally a third copolymer that is TG-poly($C_{2-3}$ akylene glycol)-PBAP-poly($C_{2-3}$ akylene glycol)-TG wherein TG at each occurrence is independently a targeting ligand, a cell penetrating peptide, an imaging agent, reactive functional group or a capping group, provided that a plurality of TG groups is a targeting ligand. The imaging agent may also be attached to amino groups within or attached to the backbone of the PBAP copolymers, or attached directly to the payload. The reactive functional group may be a group that may undergo further covalent modification such as a hydroxyl, amino, carboxyl, N-hydroxysuccinyl, maleimide, azide, alkyne or the like. The capping group may be a hydrogen, an alkyl group or other unreactive group. One or more of the first, second, and/or third copolymers include an endosomal escape group having a pKa of about 4.5 to about 6.5. Optionally, one or more of the first, second, and/or third copolymers comprises host and guest non-covalent crosslinkers. It will be understood that the plurality of copolymers in any particular polyplex is not only a mixture of the three foregoing types of copolymers, but that each type of copolymer may and typically will be a mixture of species that may differ by size and/or numbers of amino groups, endosomal escape groups, host/guest crosslinkers, and for the third copolymer, differing poly($C_{2-3}$ akylene glycol) and terminal groups.

The endosomal escape group may include a heteroaryl group having a pKa of about 4.5 to about 6.5. For example, the endosomal escape group may include an imidazolyl, pyridinyl, picolinyl, lutidinyl, indolinyl, tetrahydroquinolinyl, or quinolinyl group. In some embodiments, the endosomal escape group includes an imidazolyl group. In some embodiments, the endosomal escape group has one of the following formulae (A, B, or C):

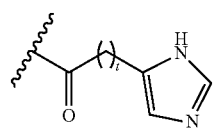

A

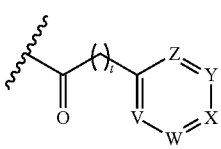

B

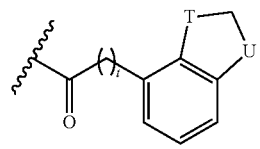

C wherein
t at each occurrence is independently 0, 1, 2 or 3
one of T and U is NH and the other is $CH_2$;
one of V, W, X, Y, Z is N and the rest are selected from CH or $CCH_3$.

The host and guest non-covalent crosslinkers include pairs of molecules that can bind to each other non-covalently by host-guest interactions and may be attached to the first, second, and/or third copolymers. For example, a residue including a cyclodextrin may be used with another residue including an adamantane. In some embodiments, the cyclodextrin is a β-cyclodextrin. In some embodiments, the β-cyclodextrin may have seven glucose subunits. Other suitable host and guest non-covalent crosslinkers may include a β-cyclodextrin and an azobenzene, or a cucurbituril and a xylylenediammonium, or a calixarene and a benzotrifluoride. In some embodiments, the guest and host non-covalent crosslinkers have the formulae:

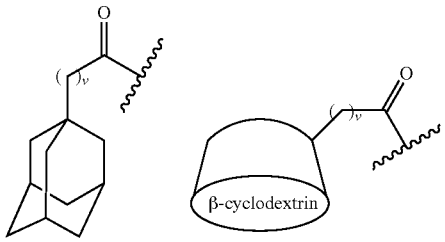

wherein v at each occurrence is 0, 1, 2, or 3. In some such embodiments, v is 1 or 2.

In some embodiments of the present technology, the first copolymer has the structure of Formula I:

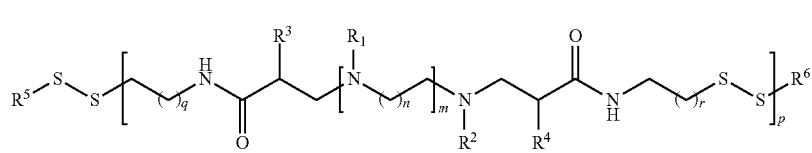

(I)

wherein
$R^1$ and $R^2$ at each occurrence are independently selected from H, a $C_{2-5}$ alkyl amino group (which may optionally be protected by an amino protecting group), a $C_{2-5}$ alkyl amino group covalently linked to the endosomal escape group or to a host or guest non-covalent crosslinker, provided that at least one occurrence of $R^1$ and $R^2$ is a $C_{2-5}$ alkyl amino group covalently linked to the endosomal escape group in each subunit present p times;

$R^3$ and $R^4$ at each occurrence are independently selected from H or $C_{1-4}$ alkyl;

$R^5$ and $R^6$ are independently —$CH_2(CH_2)_{1-4}NHC(O)$—$CHR^4$=$CH_2$;

n at each occurrence is independently 1, 2, 3, or 4;

m at each occurrence is independently 1, 2, or 3;
p is an integer from 10 to 300; and
q and r at each occurrence are independently 1, 2, 3, or 4.

In some embodiments, the second copolymer is present and has the structure of Formula II:

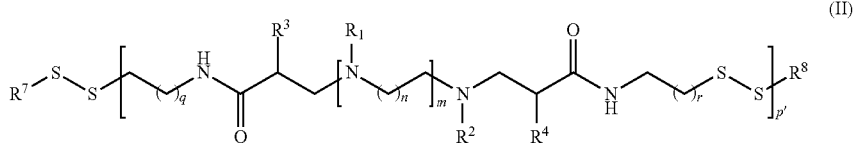

(II)

wherein
$R^1$ and $R^2$ at each occurrence are independently selected from H, a $C_{2-5}$ alkyl amino group (which may optionally be protected by an amino protecting group), a $C_{2-5}$ alkyl amino group covalently linked to the endosomal escape group or a host and/or guest non-covalent crosslinker, provided that at least one occurrence of $R^1$ and $R^2$ is a $C_{2-5}$ alkyl amino group covalently linked to the endosomal escape group in each sub unit present p times;
$R^3$ and $R^4$ at each occurrence are independently selected from H or $C_{1-4}$ alkyl;
$R^7$ and $R^8$ are independently —$[CH_2CH_2O]_x$—$R^a$ or —$[CH_2CH(CH_3)O]_x$—$R^a$;
$R^a$ at each occurrence is H or a $C_{1-6}$ alkyl group;
n at each occurrence is independently 1, 2, 3, or 4;
m at each occurrence is independently 1, 2, or 3;
p' is an integer from 10 to 300;
q and r at each occurrence are independently 1, 2, 3, or 4; and
x at each occurrence is independently 2 to 500.

In some embodiments, the third copolymer is present in the polyplex and has the structure of Formula III:

n at each occurrence is independently 1, 2, 3, or 4;
m at each occurrence is independently 1, 2, or 3;
p" is an integer from 10 to 300 or 10 to 25;
q and r at each occurrence are independently 1, 2, 3, or 4; and

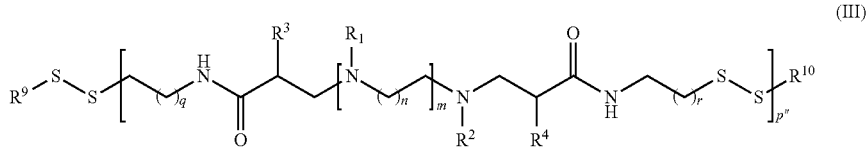

(III)

x at each occurrence is independently 2 to 500.

The present polyplexes include at least the first copolymer, e.g., a copolymer of formula I. The polyplexes may optionally include the second and/or third copolymers as well. Thus, e.g., the present polyplexes may include copolymers of Formulae I and II, I and III, or I, II, and III. Of course the present technology provides the individual copolymers of Formulae I, II, and III as well. In one aspect, at least one of $R^1$ and $R^2$ in Formulae I, II, and/or III is a $C_{2-5}$ alkylamino group in which the amino is protected by an amino protecting group, such as but not limited to trifluoroacetyl, acetyl, Boc, Cbz, Fmoc and benzoyl. In some embodiments, all of $R^1$ and $R^2$ in Formulae I, II, and/or III are a $C_{2-5}$ alkylamino group in which the amino is protected by an amino protecting group.

In some embodiments of polyplexes in which the copolymers have the structures of Formulas I, II, and/or III, instances of $R^1$ and $R^2$ may be selected from a $C_{2-5}$ alkyl amino group (which may optionally be protected by an amino protecting group), a $C_{2-5}$ alkyl amino group covalently linked to the endosomal escape group or to a host or guest non-covalent crosslinker, provided that at least one occurrence of $R^1$ and $R^2$ is a $C_{2-5}$ alkyl amino group wherein
$R^1$ and $R^2$ at each occurrence are independently selected from H, a $C_{2-5}$ alkyl amino group (which may optionally be protected by an amino protecting group), a $C_{2-5}$ alkyl amino group covalently linked to the endosomal escape group or a host and/or guest non-covalent crosslinker, provided that at least one occurrence of $R^1$ and $R^2$ is a $C_{2-5}$ alkyl amino group covalently linked to the endosomal escape group in each subunit present p times;
$R^3$ and $R^4$ at each occurrence are independently selected from H or $C_{1-4}$ alkyl;
$R^9$ and $R^{10}$ are independently —$[CH_2CH_2O]_x$—$R^b$ or —$[CH_2CH(CH_3)O]_x$—$R^b$;
$R^b$ at each occurrence is H, a $C_{1-4}$ alkyl group, a $C_{2-4}$ alkyl group substituted with a functional group selected from an $NH_2$, COOH, maleimide, N-hydroxysuccinimide, isocyanate, azide, or alkyne group, a targeting ligand, cell penetrating peptide, or an imaging agent;

covalently linked to the endosomal escape group in each subunit present p, p' or p" times. In some embodiments, at each occurrence, $R^1$ and $R^2$ are independently a $C_2$, $C_3$, or $C_4$ alkyl amino group, or a $C_2$, $C_3$, or $C_4$ alkyl amino group covalently linked to the endosomal escape group or a host-guest non-covalent crosslinker.

In some embodiments, one or more occurrences of $R^1$ and $R^2$ at each occurrence are selected from a $C_{2-5}$ alkyl amino group covalently linked to the endosomal escape group and one or more occurrences of $R^1$ and $R^2$ are selected from a $C_{2-5}$ alkyl amino group covalently linked to a host and/or guest non-covalent crosslinker. In certain embodiments, one or more occurrences of $R^1$ and $R^2$ are selected from a $C_{2-3}$ alkyl amino group covalently linked to the endosomal escape group, and one or more occurrences of $R^1$ and $R^2$ are selected from a $C_{2-3}$ alkyl amino group covalently linked to a host or guest non-covalent crosslinker. In some occurrences $R^1$ and $R^2$ are ethyl amino groups covalently linked to the endosomal escape group, and in some occurrences $R^1$ and $R^2$ are an ethyl amino group covalently linked to a host and/or guest non-covalent crosslinker.

In polyplexes in which the copolymers have the structures of Formulas I, II, and/or III, it will be understood that in some embodiments, the polyplex may comprise mixtures of the individual copolymers. For example, the polyplex may include mixtures of copolymers having different $R^1$ and $R^2$ groups. In some embodiments, 10% to 100% of the sum total of instances of $R^1$ and $R^2$ may be selected from H or a $C_{2-5}$ alkyl amino group. For example, 10%, 20%, 30%, 40%, 50%, 60%, 70%, 80% 90%, 95%, 100% or a range between and including any two of the foregoing values of instances of $R^1$ and $R^2$ may be selected from H or a $C_{2-5}$ alkyl amino group. In some embodiments of the polyplexes in which the copolymers have the structures of Formulas I, II, and/or III, 5% to 100% of the sum total of instances of $R^1$ and $R^2$ may be selected from a $C_{2-5}$ alkyl amino group covalently linked to the endosomal escape group. For example, 5%, 10%, 20%, 30%, 40%, 50%, 60%, 70%, 80% 90%, 100% or a range between and including any two of the foregoing values of instances of $R^1$ and $R^2$ are selected from a $C_{2-5}$ alkyl amino group covalently linked to the endosomal escape group. In some embodiments of the polyplexes in which the copolymers have the structures of Formulas I, II, and/or III, 5% to 90% of the sum total of instances of $R^1$ and $R^2$ may be selected from a $C_{2-5}$ alkyl amino group covalently linked to a host and/or guest non-covalent crosslinker. In some embodiments 5%, 10%, 20%, 30%, 40%, 50%, 60%, 70%, 80% 90%, or a range between and including any two of the foregoing values of instances of $R^1$ and $R^2$ may be selected from a $C_{2-5}$ alkyl amino group covalently linked to a host and/or guest non-covalent crosslinker. In some embodiments, the copolymer of Formula I, II, or III include a crosslinker, but any particular copolymer only comprises host crosslinkers or only comprises guest crosslinkers, and the polyplex will contain a mixture of the two types of copolymers of Formula I, Formula II and/or Formula III so that crosslinking can occur. For example in some instances, the molar ratio of copolymers (e.g., copolymer of Formula I) having only host crosslinkers to copolymers having only guest crosslinkers is about 1:1. In some such embodiments, the copolymers (of, e.g., Formula I) will also have instances of $R^1$ and $R^2$ selected from a $C_{2-5}$ alkyl amino group covalently linked to the endosomal escape group.

In polyplexes in which the copolymers have the structures of Formulas I, II, and/or III, in some embodiments, $R^3$ and $R^4$ at each occurrence are independently selected from H or methyl. In certain embodiments, $R^3$ and $R^4$ at each occurrence are H.

In some embodiments of polyplexes in which the copolymers have the structures of Formulas I, II, and/or III, $R^5$ and $R^6$ are independently —CH$_2$(CH$_2$)$_{1-2}$NHC(O)—CR$^4$=CH$_2$ and $R^4$ is H or methyl. In other embodiments, $R^5$ and $R^6$ are both —CH$_2$CH$_2$NHC(O)—CH=CH$_2$.

In some embodiments, of polyplexes in which the copolymers have the structures of Formulas I, II, and/or III, $R^7$ and $R^8$ are independently —[CH$_2$CH$_2$O]$_x$—$R^a$ and $R^a$ at each occurrence is H or methyl. In certain embodiments, $R^9$ and $R^{10}$ are independently —[CH$_2$CH$_2$O]$_x$—$R^b$.

In some embodiments, of polyplexes in which the copolymers have the structures of Formulas I, II, and/or III, n at each occurrence is 1 or 2. In some embodiments, m at each occurrence is 1. In certain embodiments, each of q and r is 1 or 2, e.g., 1.

In some embodiments of polyplexes in which the copolymers have the structures of Formulas I, II, and/or III, p, p' and p'' are independently an integer from 10 to 300, 10 to 250, 10 to 200, 10 to 150, 10 to 100, 10 to 75, 10 to 50, 10 to 35, 10 to 25, or 15 to 20 (i.e., 15, 16, 17, 18 or 19).

In polyplexes in which the copolymers have the structures of Formulas I, II, and/or III, in some embodiments, the host/guest non-covalent crosslinker is an β-cyclodextrin/adamantane pair.

In polyplexes in which the copolymers have the structures of Formulas I, II, and/or III, in some embodiments, the endosomal escape group is an imidazole group. The imidazole group may, e.g., be covalently linked to the first, second, and/or third copolymer via an amide group.

As noted above, the third copolymer may include a targeting ligand, a cell penetrating peptide, an imaging agent, or a capping group. The targeting ligand of the third copolymer may be selected from the group consisting of cofactors, aptamers, carbohydrates, peptides, and proteins such as antibodies and nanobodies. In some embodiments, the imaging agent is selected from the group consisting of fluorescent dyes and radioisotope-chelants.

The polyplex includes the first, second and optionally, the third formulation copolymers as described herein. In some embodiments, the weight ratio of first copolymer to second copolymer ranges from 1:1 to 5:1, and may be, e.g., 1:1, 3:2, 2:1, 5:2, 3:1, 4:1, 5:1, or a range between and including any two of the foregoing ratios. In certain embodiments, the weight ratio of first copolymer to the payload ranges from 2:1 to 100:1, and may be in some instances 2:1, 3:1, 4:1, 5:1, 10:1, 15:1, 20:1, 25:1, 30:1, 40:1, 50:1, 60:1, 70:1, 80:1, 90:1, 100:1, or a range between and including any two of the foregoing ratios. In some embodiments, the weight ratio of second copolymer to payload may be from 1:1 to 20:1. For example, the weight ratio of second copolymer to the payload can be 1:1, 2:1, 3:1, 4:1, 5:1, 6:1, 8:1, 10:1, 12:1, 14:1, 16:1, 18:1, 20:1, or a range between and including any two of the foregoing ratios. When a third copolymer is included in the polyplex, the molar ratio of first to third copolymer may range from 2:1 to 100:1 and may be in some instances 2:1, 3:1, 4:1, 5:1, 10:1, 15:1, 20:1, 25:1, 30:1, 40:1, 50:1, 60:1, 70:1, 80:1, 90:1, 100:1, or a range between and including any two of the foregoing ratios.

In another aspect, the present technology provides methods of delivering a payload to a target cell. The methods include exposing the targeted cell to any of the herein-described polyplexes. The methods include both in vitro and in vivo methods. For example, the methods may include administering any of the herein-described polyplexes to a subject in need thereof (i.e., a subject in need of the payload to be delivered by the polyplex). As used herein, a "subject" is a mammal, such as a cat, dog, rodent or primate. In some embodiments, the subject is a human. In some embodiments, the payload is any of those described herein, including but not limited to pDNA, mRNA, siRNA, Cas9 RNP, or S1mplex.

The compositions described herein can be formulated for various routes of administration, for example, by parenteral, intravitreal, intrathecal, intracerebroventricular, rectal, nasal, vaginal administration, direct injection into the target organ, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the polyplexes described herein. Injectable forms may be prepared with acceptable solvents or vehicles including, but not limited to sterilized water, phosphate buffer solution, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Exemplary carriers and excipients may include but are not limited to USP sterile water, saline, buffers (e.g., phosphate, bicarbonate, etc.), tonicity agents (e.g., glycerol), Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the present polyplexes to the patient and may include 0.1, 0.2, 0.3, 0.4, 0.5, 0.75, 1.0, 1.5, 2.0, 2.5, 3.0, 4.0, 5.0, 6.0, 7.0, 8.0, 9.0, 10, 11, 12, 13, 14, 15 mg/kg or a range between and including any two of the forgoing values such as 0.1 to 15 mg/kg. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In another aspect, the present technology provides kits including the components needed to prepare any of the compositions described herein. For example, a kit may include a package containing cationic redox-responsive copolymers as described herein and directions for use of the kit. In another embodiment, the kit includes a therapeutic payload as described herein (including but not limited to pDNA, mRNA, Cas9 polypeptide or RNP, or S1mplex) and the cationic redox-responsive copolymers and other reagents needed for preparing a polyplexes of the present technology as well as directions for preparing the polyplexes. The user would provide the desired payload or it could be supplied with the kit. The present kits allow the user to prepare the delivery composition described herein by first mixing the payload with all the copolymers or mixing the payload with the first copolymer, waiting for a short period of time (e.g., 15 minutes to an hour, preferably about a half hour), and then adding the second copolymer, and if present, the third copolymer. The kit may supply all of the copolymers, or the user may attach targeting ligands, imaging ligands, and/or cell penetrating peptides to the third copolymer to further customize the polyplex.

The examples herein are provided to illustrate advantages of the present technology and to further assist a person of ordinary skill in the art with preparing or using the polyplexes compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations or aspects of the present technology described above. The variations or aspects described above may also further each include or incorporate the variations of any or all other variations or aspects of the present technology.

EXAMPLES

General

Materials.

Triethylenetetramine (TET), triethylamine (TEA), β-CD, 4-imidazolecarboxylic acid, N,N'-dicyclohexylcarbodiimide (DCC), N-hydroxysuccinimide (NHS), L-glutathione (reduced, GSH) and 3-[4,5-dimethylthiazol-2-yl]-2,5-diphenyl tetrazolium bromide (MTT) were purchased from Sigma-Aldrich (USA). Ethyl trifluoroacetate, N,N'-bis(acryloyl) cystamine (BAC), and 1-adamantanecarboxylic acid (AD) were purchased from TCI America (USA). 1-Ethyl-3-(3-dimethylaminopropyl)carbodiimide (EDC) was purchased from Acros (USA). A poly(ethylene glycol) (PEG) derivative, $H_2N$-PEG-$OCH_3$ (Mw=5000 Da), was purchased from JenKem Technology (USA). The nuclear localization signal (NLS) peptide (sequence: PKKKKRKV) was purchased from Abi Scientific (USA). Bovine serum albumin (BSA) was purchased from Fisher (USA). NLS-tagged Cas9 protein (sNLS-Cas9-sNLS) was purchased from Aldevron (USA).

Characterization.

The chemical structures of the polymers were analyzed by $^1$H-NMR spectroscopy. The molecular weights of the PBAP polymers were studied by gel permeation chromatography (GPC) system equipped with a refractive index detector, a viscometer detector, and a light scattering detector (Viscotek, USA). The hydrodynamic diameter and zeta potential of the polyplexes were characterized by a dynamic light scattering (DLS) spectrometer (Malvern Zetasizer Nano ZS) at a 90° detection angle with a polyplex concentration of 0.1 mg/ml. Morphologies of the polyplexes were characterized by transmission electron microscopy (TEM, Philips CM200 Ultra Twin).

Statistical Analysis.

Results are presented as mean+standard deviation (SD). One-way analysis of variance (ANOVA) with Tukey's multiple comparisons was used to determine the difference between independent groups. Statistical analyses were conducted using GraphPad Prism software version 6.

Cell Culture.

Cells were cultured in a humidified cell culture incubator (Thermo Fisher, USA) at 37° C. temperature with 5% carbon dioxide. HEK 293 cells (a human embryonic kidney embryo cell line) and RAW 264.7 cells (a mouse monocyte cell line) were purchased from ATCC (USA) and cultured with 89% DMEM medium (Gibco, USA), 10% Fetal Bovine Serum (FBS, Gibco, USA) and 1% Penicillin-Streptomycin (Gibco, USA).

Example 1: Preparation of Copolymers for Polyplex

Synthesis of N,N'-[1,2-ethanediylbis(imino-2,1-ethanediyl)]bis[2,2,2-trifluoroacetamide] (Compound 1)

Ethyl trifluoroacetate was used to protect the primary amines in TET. TET (219 mg, 1.5 mmol, 1 equiv.) and TEA (455 mg, 4.5 mmol, 3 equiv.) were dissolved in 30 ml of methanol. Ethyl trifluoroacetate (532 mg, 3.75 mmol, 2.5 equiv.) dissolved in 20 ml methanol was added dropwise to the mixture and stirred at 20° C. After 24 h, the solvent was evaporated, and the mixture was purified by silica gel flash chromatography using an eluent of 1:1 v/v ethyl acetate and methanol to yield the product as a white solid (406 mg, 80% yield). $^1$H NMR (400 MHz, DMSO-d6): δ 2.56 (s, 4H, CF$_3$CONHCH$_2$CH$_2$NHC$\underline{H}_2$C$\underline{H}_2$NHCH$_2$CH$_2$NH—COCF$_3$); δ 2.63 (t, 4H, CF$_3$CONHCH$_2$C$\underline{H}_2$NHCH$_2$CH$_2$NHC$\underline{H}_2$CH$_2$NHCOCF$_3$); δ 3.24 (t, 4H, CF$_3$CONHC$\underline{H}_2$CH$_2$NHCH$_2$CH$_2$NHCH$_2$C$\underline{H}_2$NHCOCF$_3$).

Synthesis of poly(N,N'-bis(acryloyl)cystamine-co-triethylenetetramine) (p(BAC-TET))

p(BAC-TET) was synthesized via a Michael addition reaction between Compound 1 and N,N'-bis(acryloyl)cystamine (BAC). BAC (28.6 mg, 0.11 mmol) and compound 1 (33.8 mg, 0.1 mmol) were dissolved in DMF and reacted at a 1.1:1 molar ratio at 90° C. for 96 h. Polymers were then precipitated in cold ether three times to remove any unreacted species and dried under vacuum. The precipitate was then dissolved in 1 M NaOH and stirred for 2 h to deprotect the trifluoroacetate groups. Then the polymer solution was neutralized by 1 M HCl and purified by dialysis against deionized (DI) water (molecular weight cut-off (MWCO): 2 kDa). The final p(BAC-TET) product was obtained after lyophilization. $^1$H NMR (400 MHz, DMSO-d6): δ 2.15-2.40 (m, 68H, SCH$_2$CH$_2$NHCOC$\underline{H}_2$CH$_2$(NH$_2$CH$_2$CH$_2$)NC$\underline{H}_2$C$\underline{H}_2$N(CH$_2$CH$_2$NH$_2$)CH$_2$C$\underline{H}_2$ CONHCH$_2$CH$_2$S); δ 2.52-2.96 (m, 100H, SC$\underline{H}_2$CH$_2$NHCOCH$_2$CH$_2$(NH$_2$C$\underline{H}_2$C$\underline{H}_2$)NCH$_2$CH$_2$ N(C$\underline{H}_2$C$\underline{H}_2$NH$_2$)—CH$_2$CH$_2$CONHCH$_2$C$\underline{H}_2$S); δ 3.20-3.46 (m, 70H, SCH$_2$C$\underline{H}_2$NHCOCH$_2$CH$_2$—(NH$_2$CH$_2$CH$_2$)NCH$_2$CH$_2$N(CH$_2$CH$_2$NH$_2$)C$\underline{H}_2$CH$_2$CONHC$\underline{H}_2$CH$_2$S); δ 5.55 (dd, 2H, CH1$\underline{H2}$=CH—CONH—, terminal acryloyl group); δ 6.03 (dd, 2H, CH1$\underline{H2}$=CH—CONH—, terminal acryloyl group); δ 6.11 (dd, 2H, CH1H2=C$\underline{H}$—CONH—, terminal acryloyl group).

Synthesis of PEG-p(BAC-TET)-PEG

PEG was conjugated to the terminal groups of p(BAC-TET) by Michael addition. p(BAC-TET) (15 mg, 0.0018 mmol) with protected primary amines and mPEG-NH$_2$ (22 mg, 0.0044 mmol) were dissolved in anhydrous DMF and stirred at 50° C. for 24 h. Then the polymers were precipitated in cold ether three times to remove any unreacted species and vacuum dried. The precipitate was then dissolved in 1 M NaOH and stirred for 2 h to deprotect the trifluoroacetate groups. The final PEG-p(BAC-TET)-PEG polymer solution was purified by dialysis against deionized (DI) water (molecular weight cut-off: 8 kDa) followed by lyophilization. $^1$H NMR (400 MHz, D$_2$O): δ 2.67-2.79 (m, 36H, SCH$_2$CH$_2$NHCOCH$_2$CH$_2$—(NH$_2$CH$_2$CH$_2$)NC$\underline{H}_2$C$\underline{H}_2$N(CH$_2$CH$_2$NH$_2$)—CH$_2$CH$_2$CONHCH$_2$CH$_2$S); δ 3.01-3.10 (m, 34H, SCH$_2$CH$_2$NHCOC$\underline{H}_2$CH$_2$(NH$_2$CH$_2$CH$_2$)NCH$_2$CH$_2$N(CH$_2$CH$_2$NH$_2$) CH$_2$C$\underline{H}_2$CONHCH$_2$CH$_2$S); δ 3.15-3.28 (m, 100H, SC$\underline{H}_2$CH$_2$NHCOCH$_2$CH$_2$(NH$_2$C$\underline{H}_2$C$\underline{H}_2$) NCH$_2$CH$_2$N(C$\underline{H}_2$C$\underline{H}_2$NH$_2$)CH$_2$CH$_2$CONHCH$_2$C$\underline{H}_2$S); δ 3.35-3.55 (m, 70H, SCH$_2$C$\underline{H}_2$NHCO CH$_2$C$\underline{H}_2$(NH$_2$CH$_2$CH$_2$)NCH$_2$CH$_2$N(CH$_2$CH$_2$NH$_2$)C$\underline{H}_2$CH$_2$CONHC$\underline{H}_2$CH$_2$S); δ 3.60 (s, 900H, C$\underline{H}_2$C$\underline{H}_2$O—, PEG).

Synthesis of p(BAC-TET-Im/AD) and PEG-p(BAC-TET-Im/AD)-PEG

Imidazole (Im) and adamantane (AD) groups were conjugated to either p(BAC-TET) or PEG-p(BAC-TET)-PEG by DCC/NHS catalyzed amidation. The molar feed ratio of p(BAC-TET) (or PEG-p(BAC-TET))-PEG):Im was 1:4, while the molar feed ratio of p(BAC-TET) (or PEG-p(BAC-TET)-PEG):AD was 1:5. Typically, p(BAC-TET) or PEG-p(BAC-TET)-PEG (0.0011 mmol), 4-imidazolecarboxylic acid (0.5 mg, 0.0044 mmol), 1-adamantanecarboxylic acid (1 mg, 0.0055 mmol), DCC (2.1 mg, 0.01 mmol), and NHS (1.2 mg, 0.01 mmol) were dissolved in 4 ml anhydrous DMSO and stirred at room temperature. After 24 h, the mixture was filtered through a Büchner funnel to remove the byproduct dicyclohexylurea and dialyzed against DI water (MWCO 8 kDa). PEG-p(BAC-TET-Im)-PEG for non-cross-linked polyplex was synthesized with the same PEG-p(BAC-TET))-PEG:Im feed ratio without 1-adamantanecarboxylic acid addition. $^1$H NMR: p(BAC-TET-Im/AD) (400 MHz, DMSO-d6): δ 1.61-1.81 (d, 64 C$\underline{H}$C$\underline{H}_2$, adamantane); δ 2.14-2.43 (m, 68H, SCH$_2$CH$_2$NHCOC$\underline{H}_2$CH$_2$(NH$_2$CH$_2$CH$_2$)NC$\underline{H}_2$C$\underline{H}_2$N (CH$_2$CH$_2$NH$_2$)CH$_2$C$\underline{H}_2$CONHCH$_2$CH$_2$S); δ 2.55-2.92 (m, 108H, SC$\underline{H}_2$CH$_2$NHCOCH$_2$CH$_2$ (NH$_2$C$\underline{H}_2$C$\underline{H}_2$)NCH$_2$CH$_2$N(C$\underline{H}_2$C$\underline{H}_2$NH$_2$)CH$_2$CH$_2$CONHCH$_2$C$\underline{H}_2$S); δ 3.21-3.46 (m, 70H, SCH$_2$C$\underline{H}_2$NHCOCH$_2$C$\underline{H}_2$—(NH$_2$CH$_2$CH$_2$)NCH$_2$CH$_2$N(CH$_2$CH$_2$NH$_2$)—C$\underline{H}_2$CH$_2$CONHC$\underline{H}_2$CH$_2$S); δ 5.55 (dd, 2H, CH1H2=CH—CONH—, terminal acryloyl group); δ 6.03 (dd, 2H, CH1$\underline{H2}$=CH—CONH—, terminal acryloyl group); δ 6.11 (dd, 2H, CH1H2=C$\underline{H}$—CONH—, terminal acryloyl group). δ 7.82-8.322 (m, 7H, imidazole). PEG-p(BAC-TET-Im/AD)-PEG (400 MHz, D$_2$O): δ 1.60-1.81 (d, 63 C$\underline{H}$C$\underline{H}_2$, adamantane); δ 2.65-2.80 (m, 36H, SCH$_2$CH$_2$NHCOCH$_2$CH$_2$(N$_2$CH$_2$CH$_2$)NC$\underline{H}_2$C$\underline{H}_2$N(CH$_2$CH$_2$NH$_2$)CH$_2$CH$_2$CONHCH$_2$CH$_2$S); δ 3.01-3.10 (m, 40H, SCH$_2$CH$_2$NHCOC$\underline{H}_2$CH$_2$(NH$_2$CH$_2$CH$_2$)NCH$_2$CH$_2$N(CH$_2$CH$_2$NH$_2$) CH$_2$C$\underline{H}_2$CONHCH$_2$CH$_2$S); δ 3.15-3.28 (m, 100H, SC$\underline{H}_2$CH$_2$NHCOCH$_2$CH$_2$(NH$_2$C$\underline{H}_2$C$\underline{H}_2$)N CH$_2$CH$_2$N(C$\underline{H}_2$C$\underline{H}_2$NH$_2$)CH$_2$CH$_2$CONHCH$_2$C$\underline{H}_2$S); δ 3.35-3.55 (m, 70H, SCH$_2$C$\underline{H}_2$NHCO CH$_2$C$\underline{H}_2$(NH$_2$CH$_2$CH$_2$)NCH$_2$CH$_2$N(CH$_2$CH$_2$NH$_2$)C$\underline{H}_2$CH$_2$CONHC$\underline{H}_2$CH$_2$S); δ 3.60 (s, 900H, CH$_2$CH$_2$O—, PEG); δ 7.62-8.22 (m, 7H, imidazole).

Synthesis of p(BAC-TET-Im/β-CD)

Imidazole and β-CD groups were conjugated to p(BAC-TET) by EDC/NHS catalyzed amidation in water. The feed molar ratio of p(BAC-TET): Im and p(BAC-TET): β-CD were both controlled as 1:4. p(BAC-TET) (9.4 mg, 0.0011 mmol), 4-imidazolecarboxylic acid (0.5 mg, 0.0044 mmol), β-CD (4.5 mg, 0.004 mmol), EDC (1.6 mg, 0.01 mmol), and NHS (1.2 mg, 0.01 mmol) were dissolved in 4 ml DI water and stirred at room temperature for 24 h. The final product was obtained by dialysis against DI water (MWCO 8 kDa).

p(BAC-TET-Im) for non-crosslinked polyplex was synthesized with the same p(BAC-TET)):Im feed ratio without β-CD addition. $^1$H NMR: (400 MHz, DMSO-d6): δ 2.14-2.43 (m, 68H, SCH$_2$CH$_2$NHCOCH$_2$CH$_2$(NH$_2$CH$_2$CH$_2$)NCH$_2$CH$_2$N(CH$_2$CH$_2$NH$_2$) CH$_2$CH$_2$CONHCH$_2$CH$_2$S); δ 2.58-2.92 (m, 103H, SCH$_2$CH$_2$NHCOCH$_2$CH$_2$(NH$_2$CH$_2$CH$_2$)NCH$_2$CH$_2$N(CH$_2$CH$_2$ NH$_2$)CH$_2$CH$_2$CONHCH$_2$CH$_2$S); δ 3.21-3.70 (m, 200H, SCH$_2$CH$_2$NHCO CH$_2$CH$_2$—(NH$_2$CH$_2$CH$_2$)NCH$_2$CH$_2$N(CH$_2$CH$_2$NH$_2$)—CH$_2$CH$_2$CONHCH$_2$CH$_2$S and β-CD); δ 5.55 (dd, 2H, CH1H2=CH—CONH—, terminal acryloyl group); δ 6.03 (dd, 2H, CH1H2=CH—CONH—, terminal acryloyl group); δ 6.11 (dd, 2H, CH1H2=CH—CONH—, terminal acryloyl group). δ 7.62-7.92 (m, 7H, imidazole).

Example 2: Preparation of the Non-Crosslinked and Crosslinked Polyplexes with Various Nucleic Acids and CRISPR-Cas9 Genome Editing Machinery Polymer/payload polyplexes at various weight ratios were prepared using a two-step method. To form the non-crosslinked PBAP polyplexes, a sodium acetate buffer (NaOAc, 25 mM, pH 5.5) solution of p(BAC-TET-Im) polymer (5 mg/ml) was added to a payload solution (0.5 mg/ml) with varying p(BAC-TET-Im)-to-payload weight ratios. Sodium acetate buffer (NaOAc, 25 mM, pH 5.5) was then added to adjust the payload concentration to 50 μg/ml. The mixture was vortexed for 15 s and incubated for 30 min at room temperature to form the primary polyplexes. Then a sodium acetate buffer (NaOAc, 25 mM, pH 5.5) solution of PEG-p(BAC-TET-Im)-PEG polymer (5 mg/ml) and sodium acetate buffer (NaOAc, 25 mM, pH 5.5) were added to the primary polyplex solution to keep the payload concentration at 25 μg/ml. The mixture was vortexed (15 s) and incubated (30 min) at room temperature to obtain the final non-crosslinked PBAP polyplexes. To form the crosslinked PBAP (i.e., CLPBAP) polyplexes, sodium acetate buffer (NaOAc, 25 mM, pH 5.5) solutions of p(BAC-TET-Im/β-CD) and p(BAC-TET-Im/AD) polymers (5 mg/ml) were added to a payload solution (0.5 mg/ml) with a pre-determined molar ratio of β-CD and AD as well as sodium acetate buffer (NaOAc, 25 mM, pH 5.5) to adjust the payload concentration to 50 μg/ml, followed by vortexing (15 s) and incubation (30 min) at room temperature to obtain the primary crosslinked polyplexes. Then PEG-p(BAC-TET-Im/AD)-PEG polymer solution (5 mg/ml) and sodium acetate buffer (NaOAc, 25 mM, pH 5.5) were added to the primary crosslinked polyplex solution to adjust the final payload concentration to 25 μg/ml, followed by vortexing (15 s) and incubation (30 min) at room temperature to obtain the final CLPBAP polyplexes. To complex DNA with NLS, DNA (0.5 mg/ml) was incubated with an NLS solution (1 mg/ml in NaOAc buffer) at an N/P ratio of 0.25 (the ratio of moles of the amine groups of NLS to those of the phosphate groups of DNA) for 20 min, then formed polyplexes with PBAP polymers.

To study the stability of DNA polyplexes in the presence of different polyanions including albumin, non-crosslinked and crosslinked DNA polyplexes were prepared and incubated under different conditions (i.e., cell culture medium containing 10% FBS, and 40 mg/ml BSA solution in PBS. The size change of non-crosslinked and crosslinked DNA polyplexes over time was studied by DLS.

Example 3: Polyplex Bioactivity in Delivering Polynucleic Acids and Protein Complexes with Polynucleic Acid DNA Transfection Efficiency Study.

HEK 293 cells were seeded onto a 96 well plate at the amount of 20,000 per well 24 h prior to treatment. Cell culture media volume was 100 μl/well. Cells were transfected with green fluorescence protein (GFP) plasmid (Addgene, USA, 200 ng/well) using Lipofectamine™ 2000 (Lipo 2000, Thermo Fisher, USA) loaded with DNA, non-crosslinked PBAP polyplexes with different polymer/DNA weight ratios, and crosslinked CLPBAP polyplexes with different AD:β-CD molar ratio (4:2, 4:3, 4:4, 4:5 and 4:6). An untreated group was used as the control group. Cells were harvested with 0.25% trypsin (Thermo Fisher, USA) 24 h and 48 h post-treatment, spun down, and resuspended with 500 μl PBS (Thermo Fisher, USA). GFP expression efficiencies were obtained with an Attune NxT flow cytometer system (Thermo Fisher, USA) and analyzed with FlowJo 7.6.

To study the stability of the non-crosslinked and crosslinked DNA polyplexes in the presence of GSH, the transfection experiments were carried out under similar conditions, using GSH containing media. The GSH concentration in media varied from 0.001 to 20 mM.

To study the effects of PEG and imidazole groups, two special non-crosslinked DNA polyplexes were prepared: (1) polyplexes formed by PEG-lacking p(BAC-TET-Im) polymers with a p(BAC-TET-Im):DNA weight ratio of 60:1 (i.e., the same p(BAC-TET-Im) content as the polyplex formulation with a p(BAC-TET-Im):PEG-p(BAC-TET-Im)-PEG:DNA weight ratio of 48:28:1); (2) polyplexes formed by imidazole-lacking polymers p(BAC-TET) and PEG-p(BAC-TET)-PEG. The transfection experiments were carried out under similar conditions.

mRNA Transfection Efficiency Study.

HEK 293 and RAW 264.7 cells were used as mRNA transfection model cells. 24 h before treatment, HEK 293 and RAW 264.7 cells were seeded onto a 96 well plate (20,000 per well). Cells were transfected with GFP mRNA (OZ Biosciences, USA, 200 ng/well) using Lipo 2000 loaded with mRNA, non-crosslinked PBAP and crosslinked CLPBAP polyplexes complexed with mRNA at varying polymer/mRNA weight ratios. HEK 293 cells were harvested at 4, 6, 10, 24 and 48 h with 0.25% EDTA-trypsin, while RAW 264.7 cells were harvested at the same time points by repeatedly pipetting. The cells were spun down and resuspended with 500 μL PBS. GFP expression percentages were obtained with flow cytometry and analyzed with FlowJo 7.6. In a GSH stability study, gradient concentrations of GSH (0 to 20 mM) were added into mRNA treatment solution. Then HEK 293 cells were harvested 24 h later and GFP transfection efficiencies were analyzed by flow cytometry.

RNP Genome Editing Efficiency Study.

mCherry-expressing HEK 293 cells (HEK-H2B-mCherry) were generated as described previously[1] and used as a RNP transfection cell model. 24 h prior to treatment, mCherry HEK 293 cells were seeded into a 96 well plate at 15,000 cells per well. RNP was prepared as previously reported[1], by mixing NLS-tagged Cas9 protein and in vitro transcribed sgRNA (mCherry targeting guide sequence: GGAGCCGTACATGAACTGAG) at a 1:1 molar ratio. Cells were treated with complete medium, Lipo 2000 loaded with RNP, and non-crosslinked PBAP and crosslinked CLPBAP polyplexes at varying polymer/RNP weight ratios. The amount of RNP for each treatment was maintained at 156 ng Cas9 RNP (i.e., 125 ng Cas9 protein) per well. A quantity of 100 μl of fresh culture medium was added into each well two days after treatment and thereafter, half of the culture medium was refreshed every day. Six days after treatment, cells were digested, spun down and resuspended with 500 μL PBS. The RNP gene editing efficiencies were quantified with flow cytometry and data were analyzed with FlowJo 7.6.

S1mplex Genome Editing Efficiency Study.

S1mplex is made of Cas9 protein, sgRNA with a S1m aptamer, streptavidin, and a ssODN donor template. Both S1m aptamer and ssODN can bind to streptavidin to form a complex[3]. S1mplex was prepared as reported previously by mixing the four components at 4° C. for 5 min[3]. To study the genome editing efficiency of S1mplex complexed with the non-crosslinked and crosslinked polyplexes, blue fluorescence protein (BFP) HEK 293 cells generated through Lentiviral transduction of a BFP dest clone (Addgene, Cambridge, Mass.) were employed[3]. When cells are transfected with S1mPlex containing sgRNA targeting BFP (sequence: GCTGAAGCACTGCACGCCAT) and ssODN, if precise editing occurs, the BFP is changed to GFP. BFP HEK 293 cells were seeded into a 96 well plate (15,000 per well) 24 h prior to treatment. Cells were treated with Lipo 2000 loaded with S1mplex, non-crosslinked and crosslinked polyplexes complexed with S1mplex at varying polymer-to-S1mplex ratios. For each treatment, the S1mplex dosage was kept at 235 ng/well (i.e., an equivalent Cas9 protein dosage of 125 ng/well). The gene correction efficiencies were quantified six days after treatment using flow cytometry for gain of GFP fluorescence.

Intracellular Trafficking of DNA Polyplexes.

Intracellular trafficking of DNA polyplexes were studied by confocal laser scanning microscopy (CLSM). Cy3.5-conjugated DNA was used for subcellular tracking. Crosslinked CLPBAP polyplexes were prepared with or without NLS being complexed with DNA. Twenty-four hours before treatment, HEK 293 cells were seeded into Nunc™ Lab-Tek™ II CC2™ Chamber Slide (Thermo Fisher, USA, 50,000 per well). At each time point (i.e., 0.5, 2, and 6 h) after crosslinked DNA polyplex treatment, the cells were stained with endosomes/lysosome marker LysoTracker Green DND-26 (100 nM) and nucleus marker Hoechst 33342 (5 μg/mL) for 30 min at 37° C. DNA subcellular localization images were obtained with a confocal laser scanning microscope (CLSM, Nikon, Japan).

Cell Viability of the Non-Crosslinked and Crosslinked Polyplexes with Different Types of Payload (i.e., mRNA, DNA, RNP and S1mplex).

HEK 293, mCherry HEK 293, and BFP HEK 293 cells were seeded into a 96 well plate (20,000 per well). Cells were treated with complete medium, Lipo 2000 loaded with a payload, and non-crosslinked or crosslinked polyplexes containing a specific payload (e.g., DNA/mRNA/RNP/S1mplex) fabricated as described in the transfection assays. For the non-crosslinked and crosslinked polyplexes, formulations having the highest observed transfection or genome editing efficiencies were used for the cell viability studies. Cell viability was measured using a standard MTT assay 48 h after treatment (Thermo Fisher, USA). Briefly, cells were treated with media containing 500 μg/ml MTT and incubated for 4 h. MTT containing media was aspirated. Next, the purple precipitates were dissolved in 150 μl DMSO. The absorbance at 560 nm were obtained with a micro-plate reader (GloMax®-Multi Detection System, Promega, USA).

Results and Discussion

Synthesis and Characterization of a Family of PBAP-Based Polymers

Figure 1C:
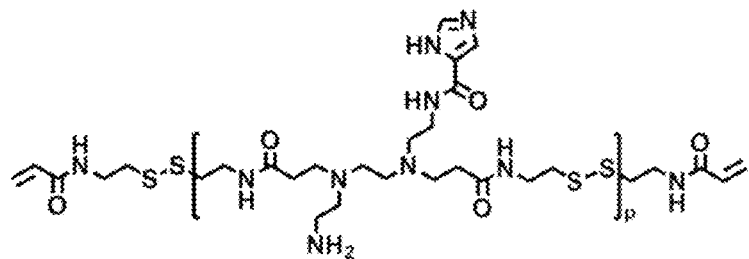
Figure 1C:
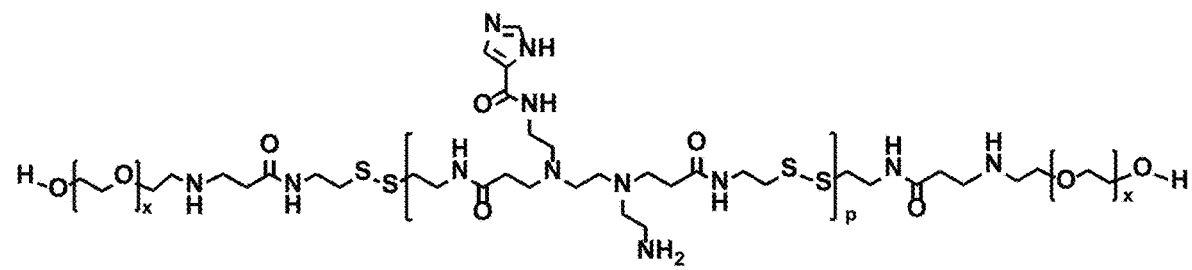
Figure 2:
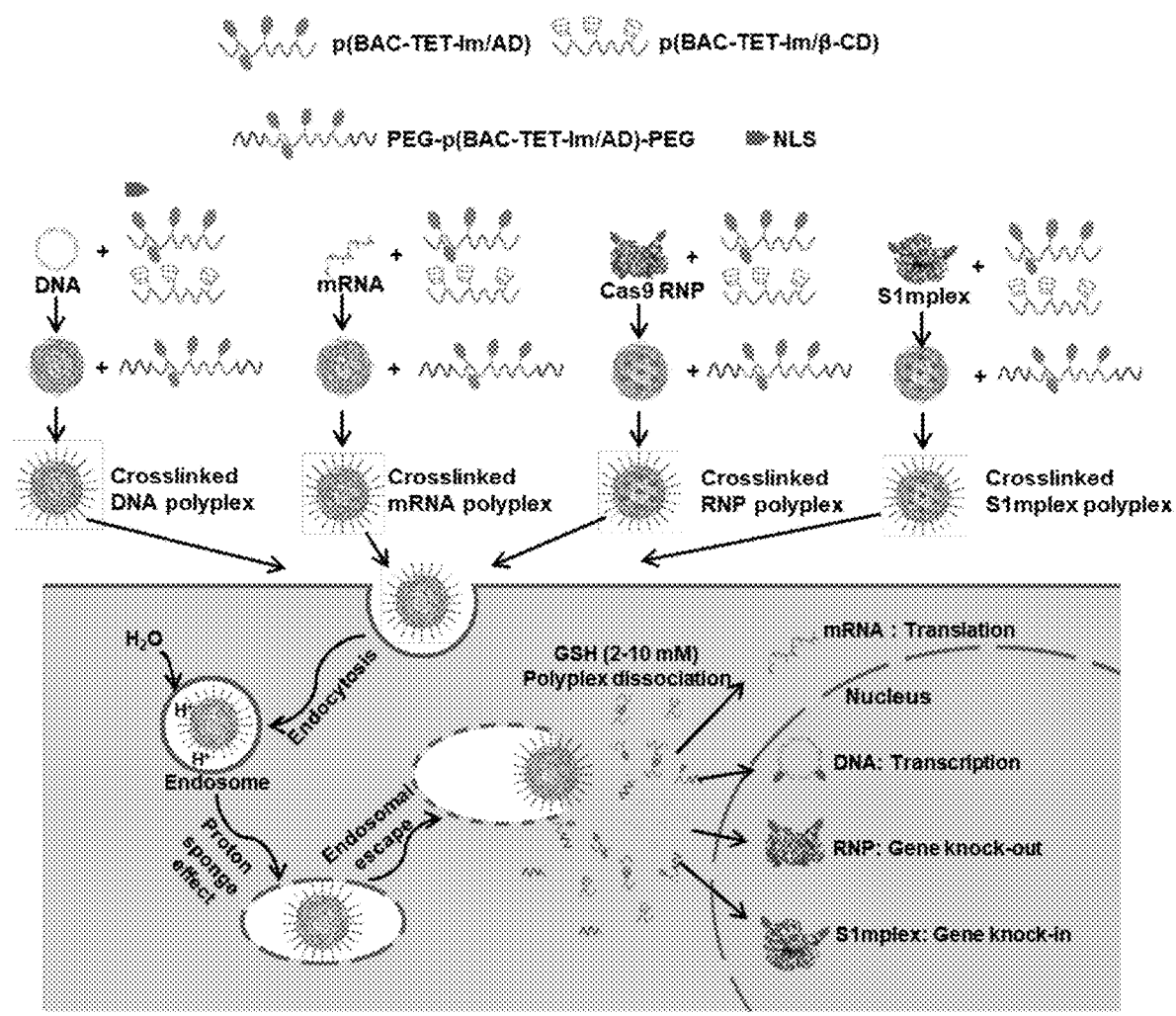
FIG. 2 shows a schematic depiction of an illustrative embodiment of the formation of crosslinked CLPBAP polyplexes and their intracellular trafficking pathways.

The non-crosslinked PBAP polyplexes were formed by p(BAC-TET-Im) (i.e., PBAP) and PEG-PBAP-PEG (FIG. 1C), while the crosslinked CLPBAP polyplexes were formed by p(BAC-TET-Im/AD) and p(BAC-TET-Im/β-CD) (i.e., CLPBAP), as well as PEG-p(BAC-TET-Im/AD)-PEG (i.e., PEG-CLPBAP-PEG) (FIGS. 1A, C and FIG. 2). Both crosslinked and non-crosslinked polyplexes were made of PBAP-based polymers containing redox-responsive disulfide bonds in the backbone to facilitate the release of payloads in the cytosol as well as imidazole groups for efficient endosomal escape. PBAP-based polymers conjugated with β-CD and AD that are capable of forming crosslinks via the host-guest interaction between β-CD and AD, were used to form the stable crosslinked polyplexes. As demonstrated in FIG. 2, once the polyplexes are taken up by cells through endocytosis, polyplexes can escape quickly from endosomal compartments due to the proton sponge effect enhanced by the imidazole groups. The polyplexes fall apart once they enter the cytosol, where the disulfide bond-containing polymer backbone is degraded by high-concentration GSH, thereby releasing the payloads. mRNA functions in cytosol, while DNA, RNP and S1mplex, facilitated by NLS, will be transported to the nucleus.

Figure 3A:
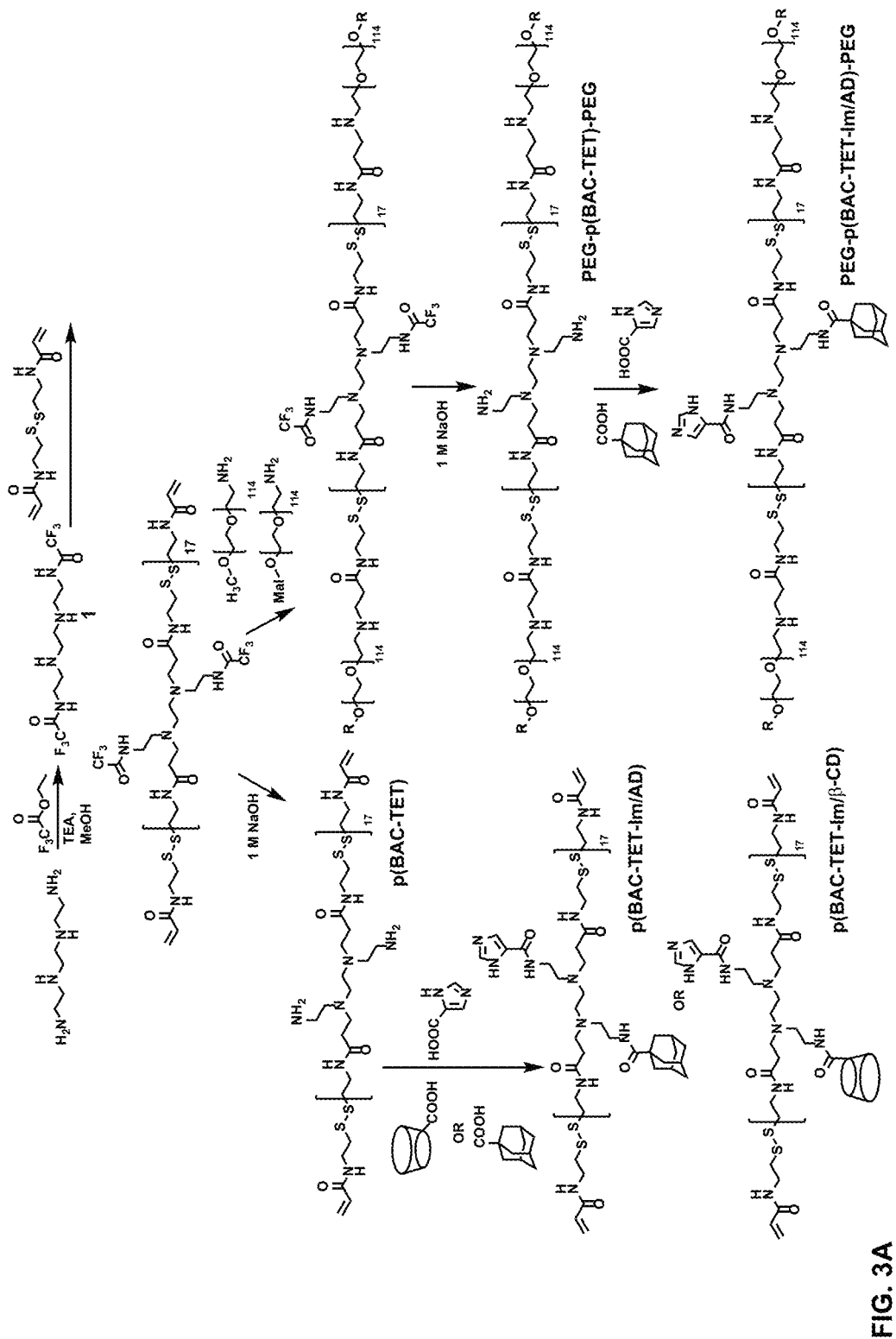
FIGS. 3A-3B show synthetic schemes for three illustrative PBAP-based polymers with host and guest non-covalent crosslinkers (i.e., CLPBAP polymers) used for forming crosslinked CLPBAP polyplexes (FIG. 3A) and two PBAP-based polymers without crosslinkers (FIG. 3B), used to form non-crosslinked polyplexes. "R" may be H or TG as defined herein.
Figure 3B:
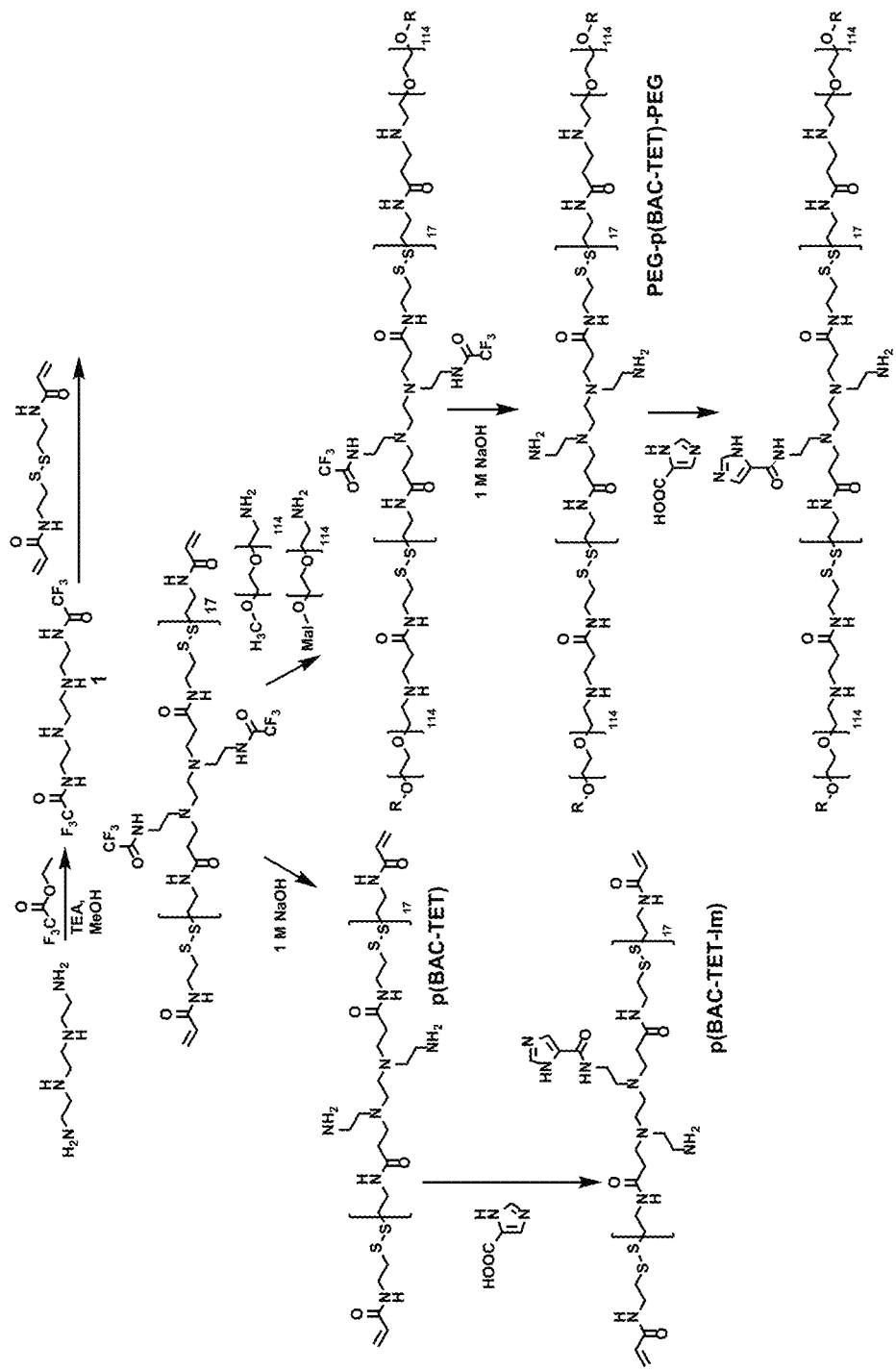

FIG. 3A shows a synthesis scheme for the three PBAP-based polymers used to form CLPBAP polyplexes. First, trifluoroacetate (TFA)-protected TET (Compound 1) was polymerized with disulfide bond-containing monomer BAC through Michael addition. To ensure both terminal groups are acrylamides, the feed molar ratio of BAC:Compound 1 was set at 1.1:1. After the removal of the TFA protecting groups, imidazole groups and crosslinking groups (i.e., AD and β-CD) were conjugated onto the p(BAC-TET) polymer via DCC/NHS catalyzed amidation to yield p(BAC-TET-Im/AD) and p(BAC-TET-Im/β-CD). To synthesize the PEG-p(BAC-TET)-PEG polymers, methoxy(m)PEG-NH$_2$ was conjugated to TFA-protected PBAP polymer through Michael addition followed by TFA deprotection. To ensure that PEG-p(BAC-TET)-PEG polymer molecules can also be integrated into the crosslinked polyplexes via β-CD and AD host-guest interaction, PEG-p(BAC-TET)-PEG were conjugated with both AD and imidazole groups to form PEG-p(BAC-TET-Im/AD)-PEG. PBAP-based Polymers used to form non-crosslinked PBAP polyplexes, namely, p(BAC-TET-Im) and PEG-p(BAC-TET-Im)-PEG, were synthesized similarly without the conjugation of AD and β-CD (FIG. 3B) The chemical structures of all intermediate and final polymer products were confirmed by $^1$H NMR. The number-average molecular weight ($M_n$) of p(BAC-TET), characterized by GPC, was 8.5 kDa with a polydispersity index (PDI) of 1.6. The numbers of AD and β-CD groups conjugated onto p(BAC-TET-Im) were controlled to 4 and 3, respectively, per polymer chain, as confirmed by NMR not shown) and GPC (Table 1). It will be understood by those skilled in the art that all of the claimed copolymers of Formulas I, II and III may be prepared by similar methods, after minor adjustments in the use of amino protecting groups and the starting materials. For example, the use of Boc protecting groups on suitable starting polyamines permits the synthesis of copolymers where $R^1$ and $R^2$ are H.

TABLE 1

Molecular weights of the polymers used to form the
non-crosslinked and crosslinked polyplexes measured by GPC.

| Polymer | Number-average molecular weight ($M_n$) | Polydispersity Index (PDI) |
| --- | --- | --- |
| p(BAC-TET) | 8.5 kDa | 1.6 |
| PEG-p(BAC-TET)-PEG | 19.1 kDa | 1.7 |
| p(BAC-TET-Im/AD) | 9.2 kDa | 1.7 |
| p(BAC-TET-Im/β-CD) | 12.3 kDa | 1.9 |
| PEG-p(BAC-TET-Im/AD)-PEG | 19.5 kDa | 2.1 |

Figure 4:
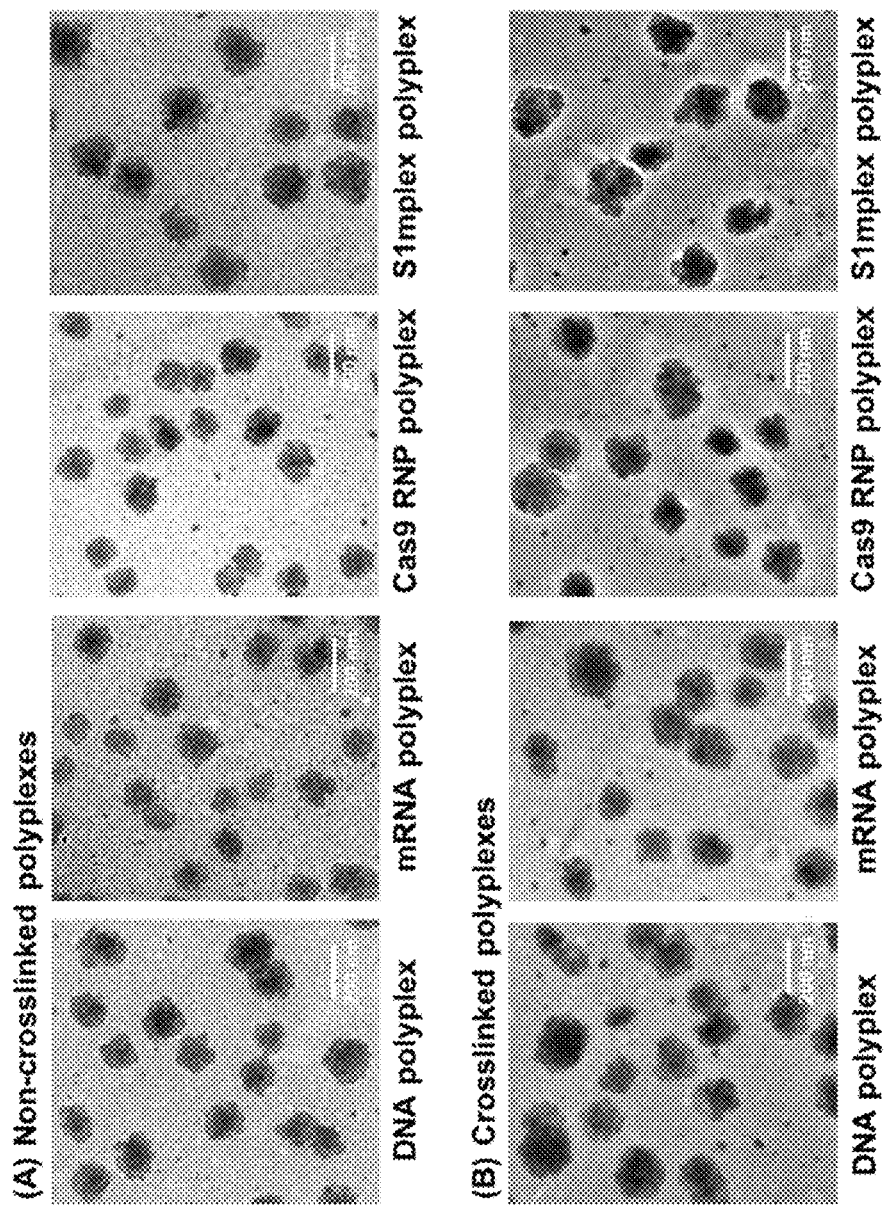
FIGS. 4A-4B. Transmission electron microscopy (TEM) images of (FIG. 4A) non-crosslinked and (FIG. 4B) crosslinked polyplexes with different payloads. From left to right: DNA, mRNA, RNP, and S1mplex.

Preparation and Characterization of the Non-Crosslinked and Crosslinked Polyplexes Non-crosslinked PBAP polyplexes were fabricated by mixing p(BAC-TET-Im) (i.e., PBAP) with payloads to form the primary polyplexes first, followed by the addition of PEG-p(BAC-TET-Im)-PEG (i.e., PEG-PBAP-PEG) to yield the final PEGylated polyplexes. To fabricate the crosslinked CLPBAP polyplexes, CLPBAP polymers (i.e., p(BAC-TET-Im/AD) and p(BAC-TET-Im/β-CD)) were mixed with payloads first and then incubated for 30 min to allow for complete complexation between AD and β-CD. Thereafter, PEG-p(BAC-TET-Im/AD)-PEG (i.e., PEG-CLPBAP-PEG) polymer was added to the primary polyplexes to yield the PEGylated crosslinked polyplexes. The sizes and morphologies of the non-crosslinked and crosslinked polyplexes with different payloads were studied by TEM as shown in FIGS. 4A and 4B, respectively. The size distribution and zeta potential of the various polyplexes were studied by DLS (Table 2). The average hydrodynamic diameters of the non-crosslinked polyplexes ranged from 136 to 151 nm, depending on the type of payload, while the average hydrodynamic diameters of the crosslinked polyplexes ranged from 168 to 191 nm. Both non-crosslinked and crosslinked polyplexes had nearly neutral surface charges with zeta potentials ranging from −1.5 to 8.6 mV.

TABLE 2

Size and zeta-potential of non-crosslinked PBAP and crosslinked CLPBAP polyplexes.

| Polyplex | Payload | Size by DLS (nm) | Zeta potential (mV) |
| --- | --- | --- | --- |
| non-crosslinked | DNA | 136 | 8.6 |
|  | mRNA | 150 | 2.0 |
|  | RNP | 143 | 6.7 |
|  | S1mplex | 151 | 3.5 |
| crosslinked | DNA | 168 | 7.9 |
|  | mRNA | 191 | −1.5 |
|  | RNP | 170 | 5.4 |
|  | S1mplex | 179 | 4.5 |

Stability Study of the Non-Crosslinked PBAP and Crosslinked CLPBAP Polyplexes.

Nanoparticles (NPs) formed by cationic polymers and cationic lipids are commonly used for delivery of negatively charged nucleic acids and proteins. However, NPs formed solely by electrostatic interactions often possess insufficient instability in vitro and in vivo. During circulation, the stability of such NPs can be affected by several factors including dilution, flow stress, and interaction with serum proteins. For instance, polyanions such as serum albumin and heparin can destabilize the NPs and cause premature release of the payloads.[2] To overcome the potentially poor stability of the non-crosslinked PBAP polyplexes, β-CD and AD were conjugated to the p(BAC-TET-Im) polymer backbone. The host-guest interactions between β-CD and AD, in addition to the electrostatic interactions, may enhance the stability of the resulting crosslinked CLPBAP polyplexes.

Figure 5:
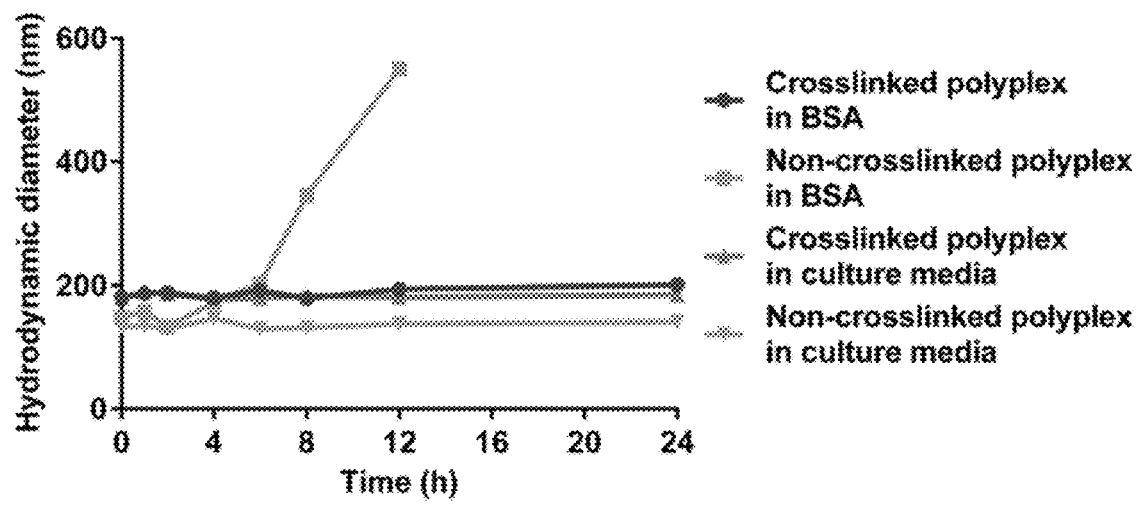
FIG. 5. Stability of non-crosslinked and crosslinked DNA polyplexes in FBS-containing cell culture media and a polyanion solution (bovine serum albumin (BSA), 40 mg/ml in PBS).

To investigate the stability of the non-crosslinked and crosslinked polyplexes against polyanions, non-crosslinked and crosslinked DNA polyplexes formed by PBAP and CLPBAP polymers, respectively, were incubated in a cell culture medium (DMEM containing 10% FBS) and a polyanion solution (BSA solution, 40 mg/ml in PBS, mimicking the albumin concentration in vivo).[3] The sizes of the polyplexes were monitored over time. As shown in FIG. 5, the sizes of both non-crosslinked and crosslinked polyplexes remained unchanged in FBS-containing cell culture media, indicating that both types of polyplexes exhibited good stability in cell culture media. However, when being exposed to a BSA solution with a BSA concentration similar to the blood albumin concentration, the size of the non-crosslinked PBAP polyplexes increased significantly after 2 h, indicating the interruption of the polyplex structure by polyanions. In contrast, the size of the crosslinked CLPBAP polyplexes did not change notably throughout the study period, indicating enhanced stability desirable for in vivo applications.

Figure 6:
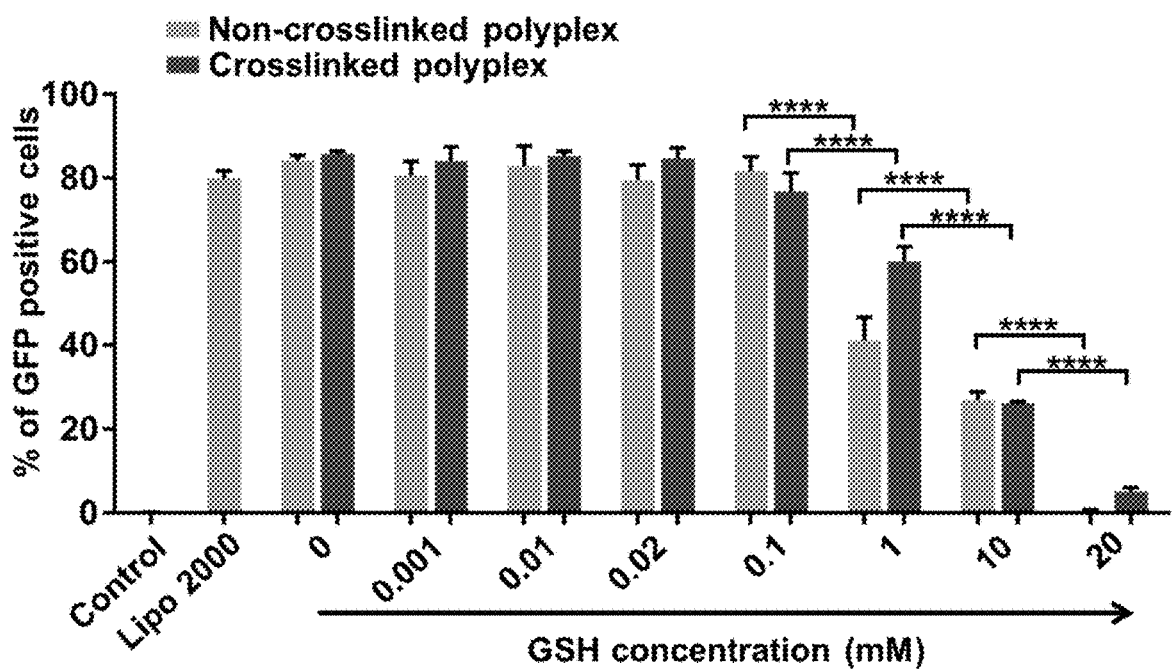
FIG. 6. Effects of GSH concentration in the cell culture media on the mRNA transfection efficiency of both crosslinked and non-crosslinked polyplexes. Non-crosslinked polyplexes were formed with a PBAP:PEG-PBAP-PEG:mRNA weight ratio of 48:28:1; while the crosslinked polyplexes were formed with a CLPBAP:PEG-CLPBAP-PEG:mRNA weight ratio of 48:28:1 and AD:β-CD molar ratio of 4:3. *: $p<0.05$; ****: $p<0.0001$; n=3.

Disulfide bonds were integrated into the PBAP-based polymer backbone to facilitate payload release into the cytosol where the GSH concentration (2-10 mM) is much higher than extracellular spaces (0.001-0.02 mM). While it is highly desirable to rapid release the payload into the cytosol of the target cell, where the payload can function (e.g., mRNA) or be transported to the nucleus (e.g., DNA, RNP, and S1mplex), it is also essential to keep the polyplexes intact in the blood stream and other extracellular spaces. To study the stability of the polyplexes at different GSH levels, GFP mRNA polyplexes were prepared and incubated with HEK 293 cells for 24 h in culture media with GSH concentrations ranging from 0-20 mM. GFP transfection efficiency was measured to determine the functionality of the polyplexes. As shown in FIG. 6, mRNA transfection was not affected at GSH concentrations lower than 0.1 mM for both non-crosslinked and crosslinked polyplexes, indicating both types of polyplexes exhibited good stability at extracellular GSH levels. A significant decrease in transfection efficiencies were observed at a GSH concentration of 1 mM or higher, suggesting that GSH induced polyplex degradation occurred in the cell culture media, which may cause mRNA release before cellular uptake. These findings have demonstrated that these GSH-responsive polyplexes are stable at extracellular matrices, but can fall apart and release payload effectively in the cytosol of the target cells.

Effects of Polyplex Formulations on DNA Delivery.

Figure 7B:
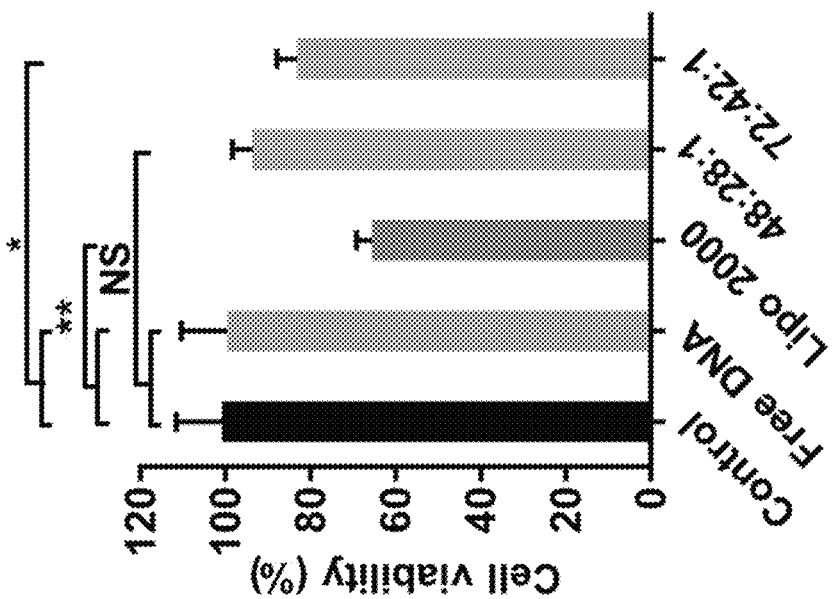
FIGS. 7A-7B.

To study the effects of various polyplex formulations on the DNA transfection efficiencies, the weight ratio of PBAP: PEG-PBAP-PEG:DNA was varied initially using the non-crosslinked polyplex NPs (FIG. 7A) in HEK 293 cells. Three weight ratios, namely, PBAP:PEG-PBAP-PEG:DNA=24: 14:1, 48:28:1, and 72:42:1, were studied. GFP-expressing DNA was used to measure the transfection efficiency of these polyplex formulations. Among the three formulations studied, the two formulations with higher PBAP polymer ratios showed comparable transfection efficiency to Lipo 2000, a commercially available liposome-based delivery system. The mean fluorescence intensity (MFI) data indicated a similar trend (data not shown). Among the three different weight ratios, the PBAP:PEG-PBAP-PEG:DNA weight ratio of 48:28:1 and 72:42:1 induced similar, but higher transfection efficiency than the PBAP:PEG-PBAP-PEG:DNA weight ratio of 24:14:1. However, the PBAP:PEG-PBAP-PEG:DNA weight ratio of 48:24:1 exhibited significantly lower cytotoxicity than the weight ratio of 72:42:1 (FIG. 7B). Therefore, the PBAP:PEG-PBAP-PEG:DNA weight ratio of 48:28:1 was used for further tests of DNA delivery.

Figure 7A:
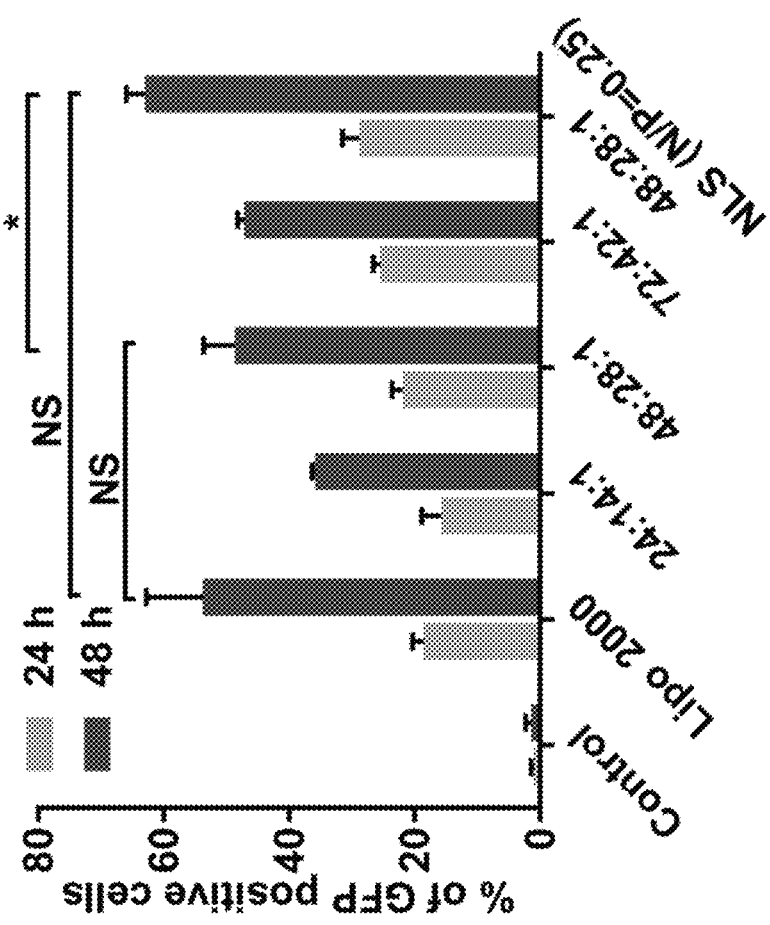
Figure 8:
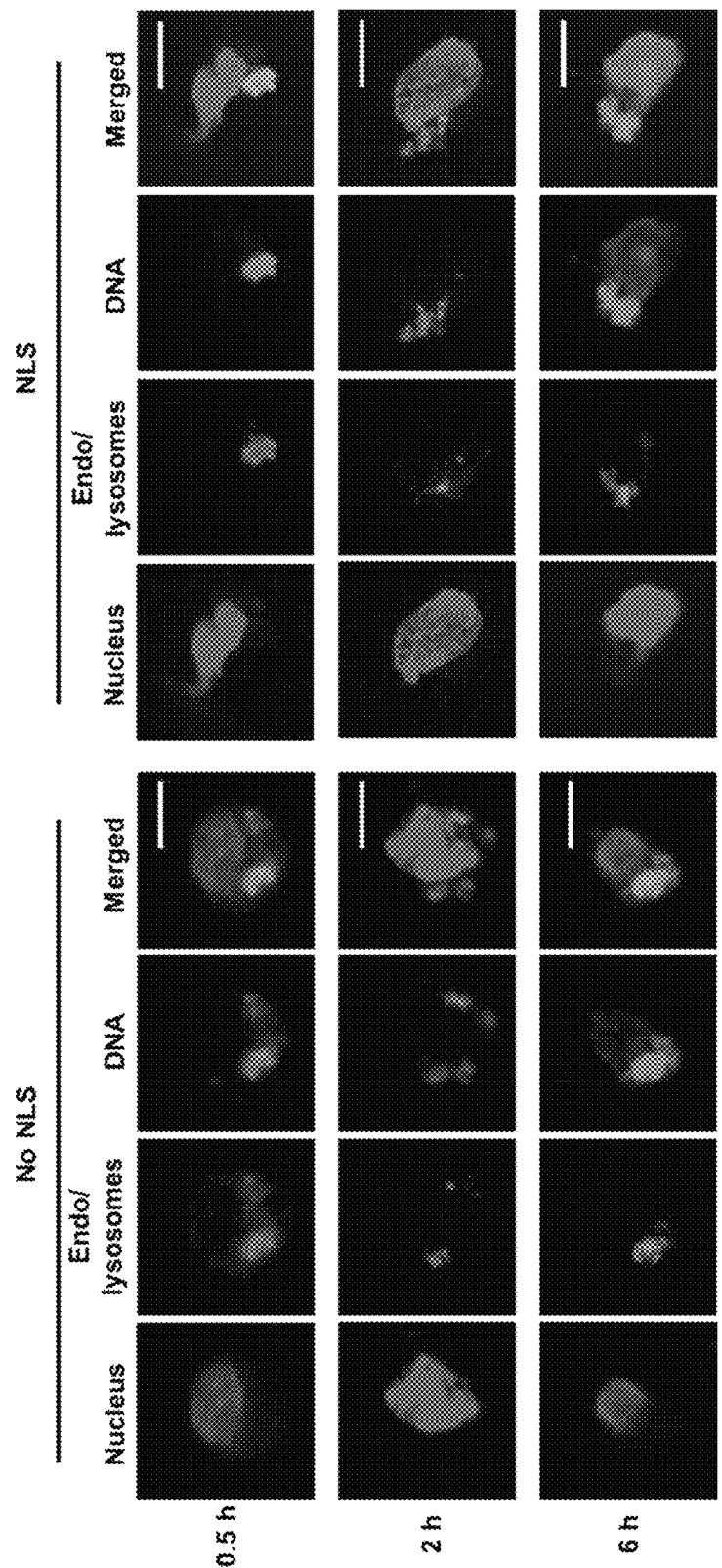
FIG. 8. Intracellular trafficking of the crosslinked DNA polyplex with and without NLS.

The intracellular trafficking pathway is important for proper function of the payload. The nuclear membrane acts as a barrier to prevent free passage of macromolecules, making nuclear entry challenging but crucial for nucleic acids and CRISPR-Cas9 genome editing machineries. To induce efficient nuclear translocation and ultimately, efficient transfection, NLS (positively charge) was complexed with negatively charged DNA through electrostatic interactions before polyplex formation. As shown in FIG. 7A, complexation of DNA with a small amount of NLS (N/P ratio=0.25) before polyplex formation can significantly enhance DNA transfection efficiency, owing to NLS's nuclear translocation capability. To study the intracellular trafficking of crosslinked DNA polyplex, imaging using CLSM was performed at different time points. As shown in FIG. 8, the co-localization of DNA and endo/lysosomes was observed as early as 0.5 h post treatment, indicating the uptake of polyplexes through endocytosis. The co-localization of DNA and endo/lysosomes considerably decreased 2 h post treatment, indicating the efficient endosomal escape capability of the polyplex facilitated by imidazole groups. The crosslinked DNA polyplexes with NLS showed greater overlapping of DNA signals and nucleus 6 h post treatment, indicating that NLS effectively facilitated the nuclear entry of DNA.

Figure 9:
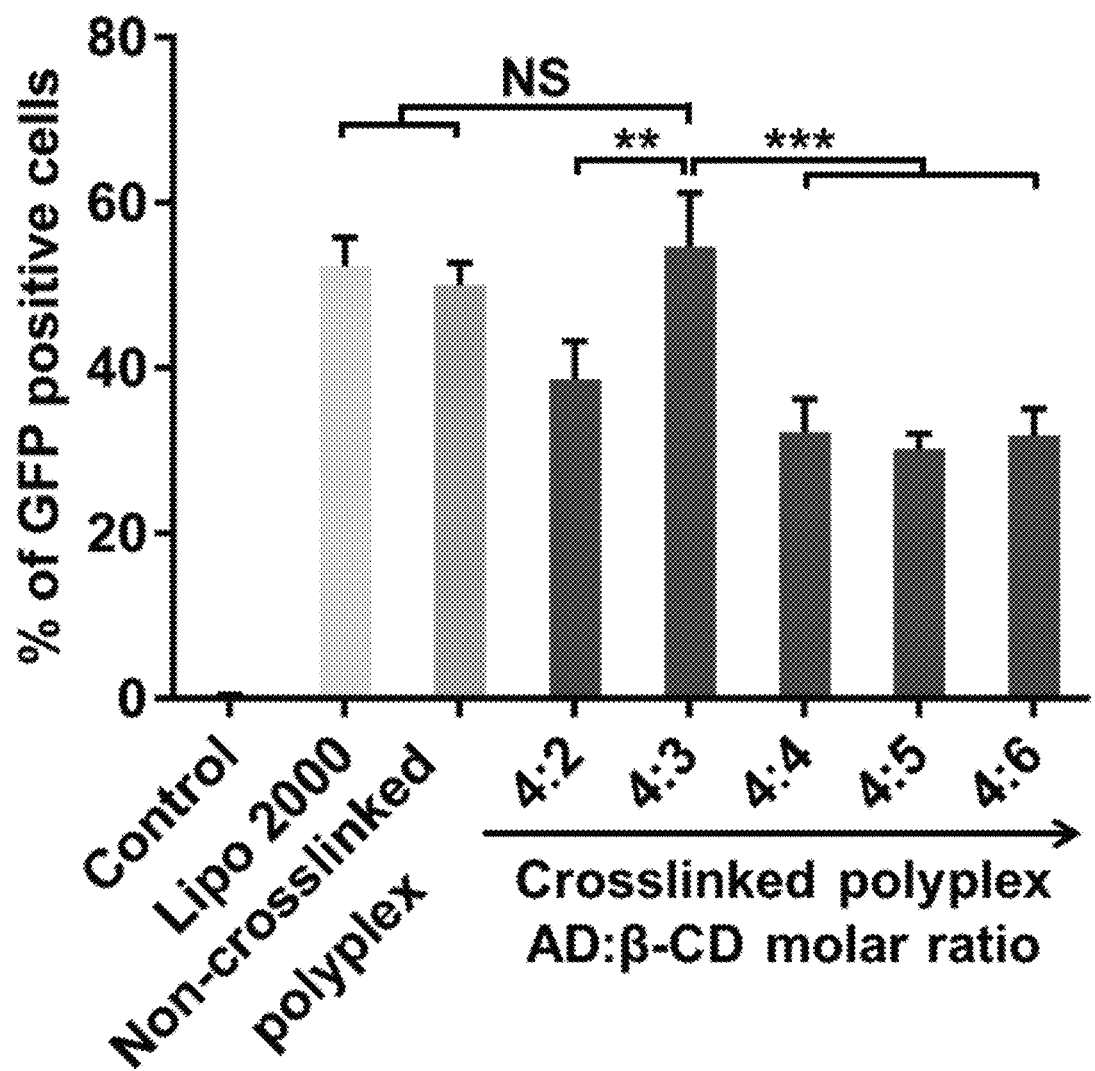
FIG. 9. Exploration of the AD:β-CD molar ratio in crosslinked CLPBAP DNA polyplexes. HEK 293 cells were treated with Lipo 2000, non-crosslinked PBAP polyplexes, and crosslinked CLPBAP polyplexes with different crosslinker molar ratios. The transfection efficiency was measured 48 h post treatment. NS: not significant, : $p<0.01$; *: $p<0.001$; n=3.

The effects of the AD:β-CD molar ratio for the crosslinked CLPBAP polyplexes were subsequently studied. By fixing the weight ratio of CLPBAP:PEG-CLPBAP-PEG:DNA to 48:24:1, the molar ratio of the crosslinkers (AD:β-CD) was adjusted from 4:2 to 4:6. As shown in FIG. 9, the highest transfection efficiency was achieved with AD:β-CD molar ratio=4:3, and the transfection efficiency of the crosslinked CLPBAP polyplexes was comparable to non-crosslinked PBAP and Lipo 2000. The MFI data also indicated a similar trend (not shown). This AD:β-CD molar ratio was used for further studies.

Figure 10A:
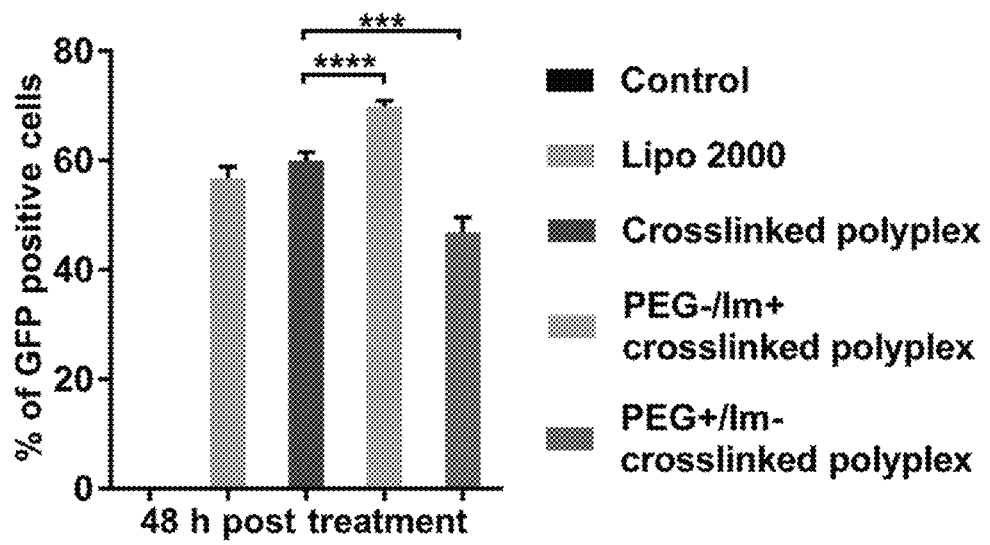
FIGS. 10A-10B. Effects of PEG and imidazole groups on the transfection efficiency of the crosslinked polyplexes.
Figure 10B:
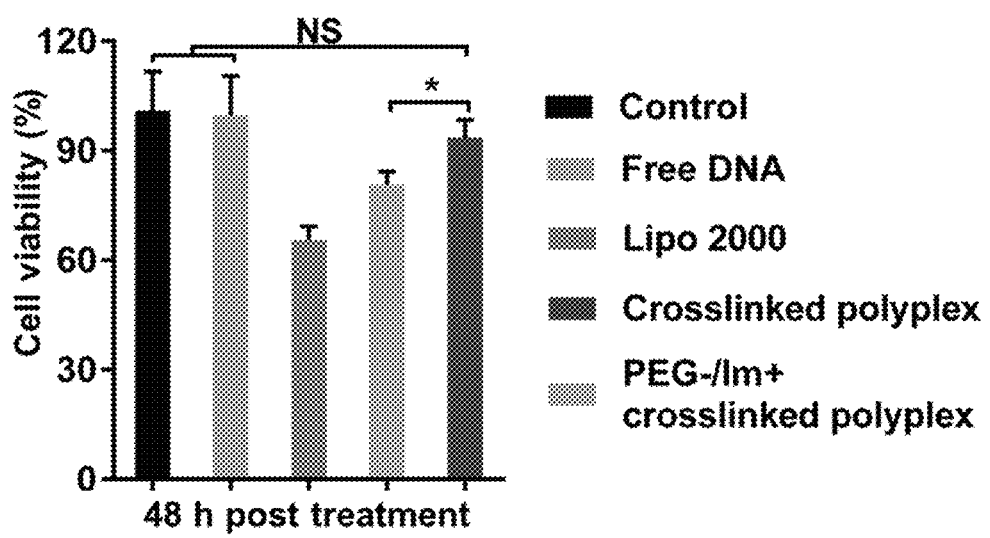

To study the function of PEG and imidazole groups in the polyplex delivery system, crosslinked CLPBAP polyplexes were prepared using PBAP-based polymers without PEG and imidazole groups, respectively. The DNA transfection efficiencies of the polyplexes were studied by flow cytometry (FIG. 10A). The crosslinked polyplexes without imidazole groups showed significantly lower transfection efficiency than those with imidazole. The enhanced transfection efficiency associated with imidazole conjugation can be attributed to the enhanced endosomal escape capability afforded by the imidazole groups, whose pKa value is around 6.0. Imidazole groups can be quickly protonated in acidic endocytic compartment, leading to the so-called proton sponge effect. We also found that crosslinked CLPBAP polyplexes without PEG (i.e., polyplexes made of CLPBAP and DNA only, without the PEG-CLPBAP-PEG component) exhibited a higher transfection efficiency, but this was accompanied with a significantly higher cytotoxicity (FIG. 10B). Without PEG on the surface of the polyplexes, the crosslinked polyplexes had a higher positive surface charge (17.2 mV), which may lead to elevated binding and endocytosis of the polyplexes by cells; however, the dense positive surface charge may also cause cell membrane disruption, leading to cell death.[4]

Figure 11A:
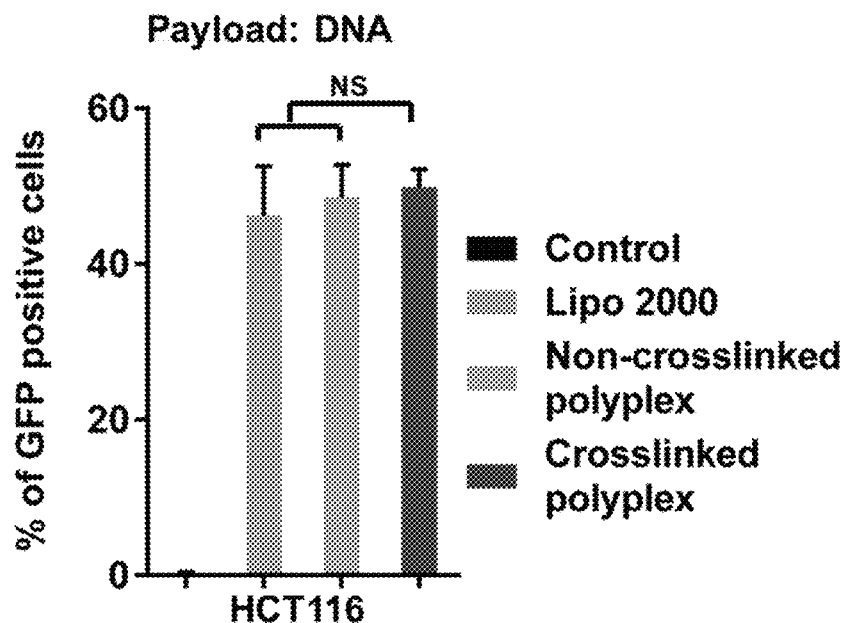
FIGS. 11A-11B. Efficient delivery of DNA by the polyplexes in multiple cell lines. Transfection efficiency of the DNA polyplexes in HCT116 cells (FIG. 11A) and NHDF cells (FIG. 11B). The weight ratios of PBAP:PEG-PBAP-PEG:DNA or CLPBAP:PEG-CLPBAP-PEG:DNA in the PBAP and CLPBAP polyplexes, respectively, were fixed at 48:24:1. The AD:β-CD molar ratio in the crosslinked PBAP polyplexes was fixed as 4:3. NS: not significant; *: $p<0.05$; n=3.
Figure 11B:
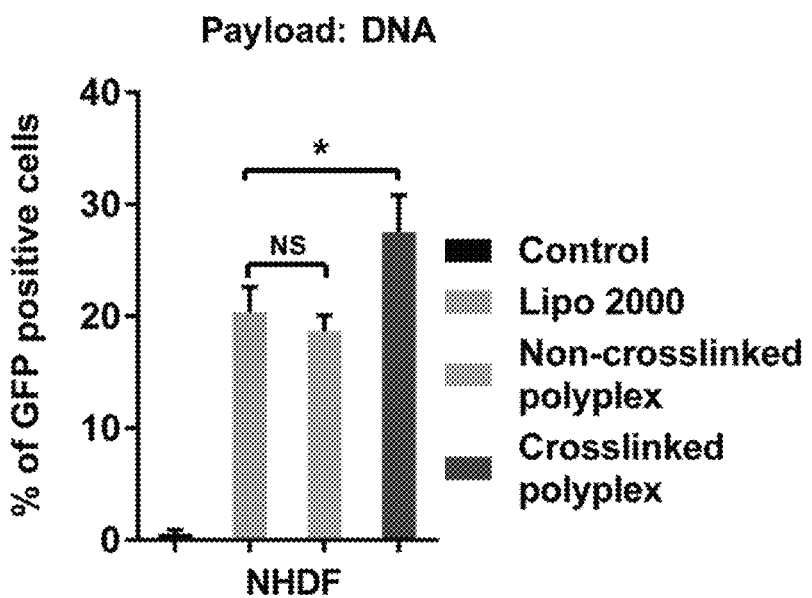

We further investigated the DNA delivery efficiency of the polyplexes in two other cell lines (i.e., HCT 116 and NHDF cells). As shown in FIGS. 11A and 11B, in both HCT116 cells, non-crosslinked and crosslinked polyplexes showed similar DNA transfection efficiencies to Lipo 2000, in NHDF cells, crosslinked PBAP polyplexes induced higher DNA transfection efficiencies than non-crosslinked PBAP polyplexes and Lipo 2000, while non-crosslinked polyplexes showed similar DNA and mRNA transfection efficiencies to Lipo 2000. These results suggest that both non-crosslinked and crosslinked polyplexes are suitable for DNA delivery in a variety of cells.

mRNA Delivery Studies.

Figure 12A:
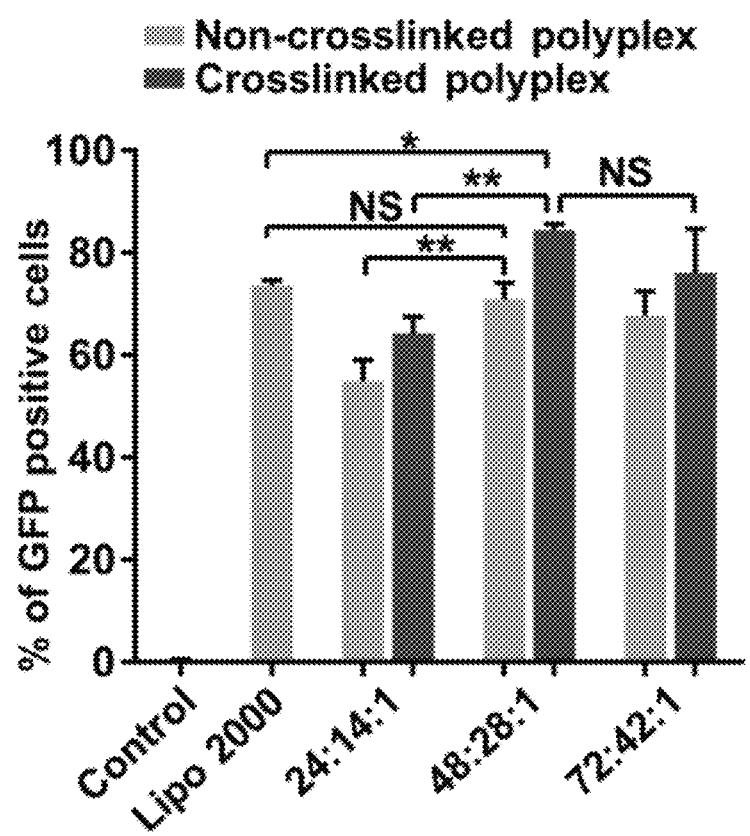
FIGS. 12A-12C (FIG. 12A) Exploration of PBAP-based polymers and mRNA weight ratios for mRNA transfection. HEK293 cells were treated with Lipo 2000, non-crosslinked polyplexes with three different PBAP:PEG-PBAP-PEG:mRNA weight ratios, and crosslinked polyplexes with three different CLPBAP:PEG-CLPBAP-PEG:mRNA weight ratios. In the crosslinked polyplexes, the AD:β-CD molar ratio was fixed at 4:3.
Figure 12B:
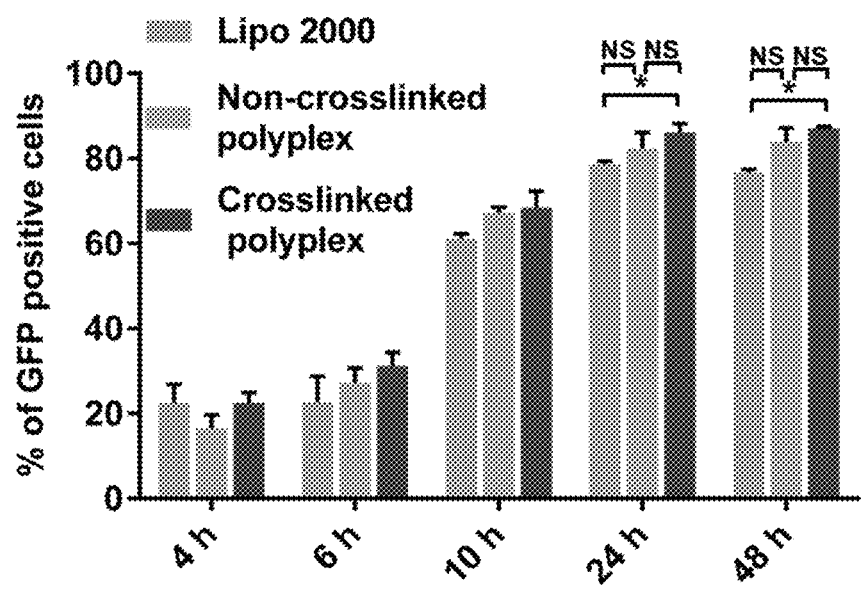
Figure 12C:
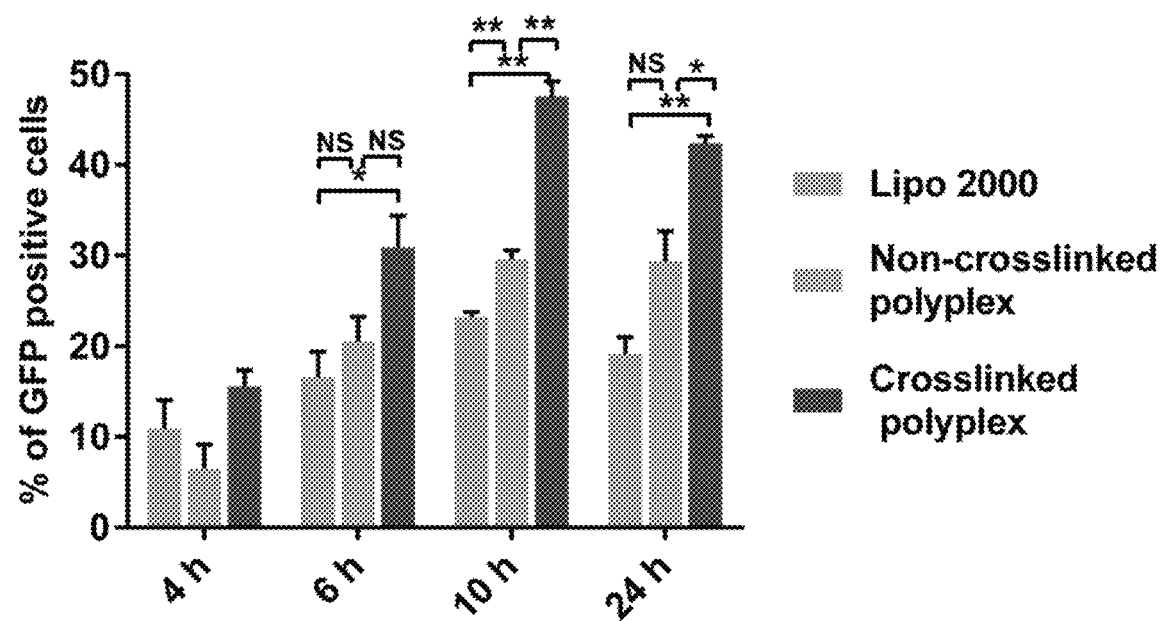

The weight ratio between the PBAP-based polymers and mRNA was first explored (FIG. 12A) using GFP mRNA, and the formulations with the highest transfection efficiency for non-crosslinked (PBAP: PEG-PBAP-PEG:mRNA=48:28:1) and crosslinked (CLPBAP: PEG-CLPBAP-PEG:mRNA=48:28:1) were used for further studies. The transfection efficiencies of both non-crosslinked and crosslinked mRNA polyplexes were studied in two cell lines (HEK 293 and RAW 264.7), as shown in FIGS. 12B and 12C, respectively. In HEK 293 cells, GFP expression was detected as early as 4 h post treatment and peaked at 24 h; in RAW 264.7 cells, GFP expression reached a plateau much earlier at 10 h. The non-crosslinked PBAP polyplexes exhibited comparable transfection efficiencies to Lipo 2000 in HEK 293 cells, and higher transfection efficiencies in RAW 264.7 cells 10 h post treatment. The crosslinked CLPBAP polyplexes exhibited higher transfection efficiencies than Lipo 2000 in both cell lines, particularly in RAW 264.7 cells, where they showed an approximately 2-fold higher transfection efficiency. In HEK 293 cells, the transfection efficiencies of non-crosslinked and crosslinked polyplexer were similar; however, in Raw 264.7 cells, the crosslinked polyplexes exhibited an approximately 1.5-fold higher transfection efficiency. The MFI data also exhibited a similar trend (data not shown).

Figure 13A:
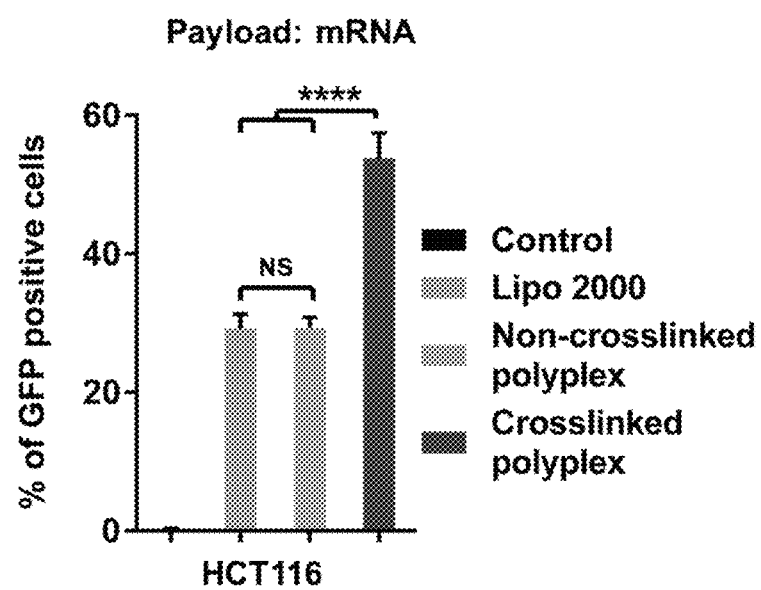
FIGS. 13A-13B. Efficient delivery of mRNA by the polyplexes in multiple cell lines. Transfection efficiency of the DNA polyplexes in HCT116 cells (FIG. 13A) and NHDF cells (FIG. 13B). The weight ratios of PBAP:PEG-PBAP-PEG:mRNA or CLPBAP:PEG-CLPBAP-PEG:mRNA in the PBAP and CLPBAP polyplexes, respectively, were fixed at 48:24:1. The AD:β-CD molar ratio in the crosslinked PBAP polyplexes was fixed as 4:3. NS: not significant; : $p<0.01$; **: $p<0.0001$; n=3.
Figure 13B:
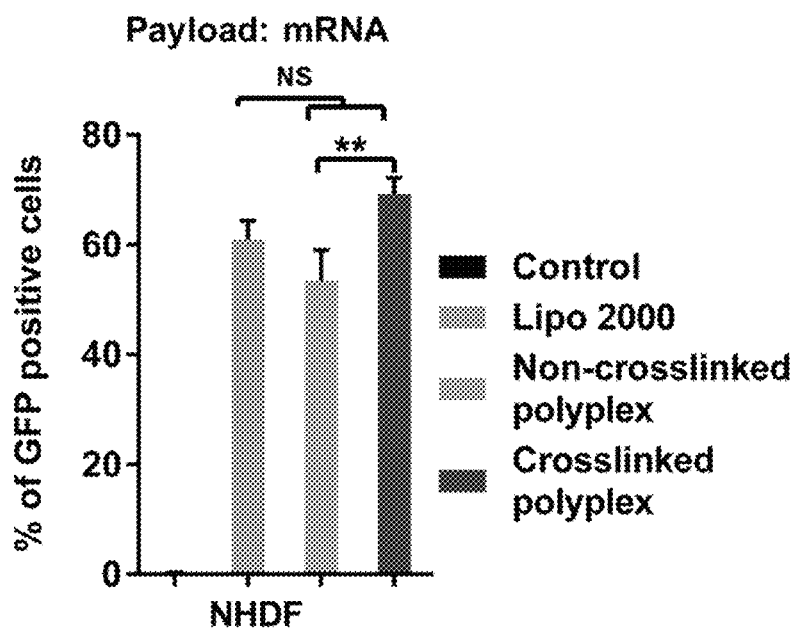

We further investigated the mRNA delivery efficiency of the polyplexes in two other cell lines (i.e., HCT 116 and NHDF cells). As shown in FIGS. 13A and 13B, in HCT116 cells, a significantly higher mRNA transfection efficiency was observed with the crosslinked CLPBAP polyplexes. In NHDF cells crosslinked PBAP polyplexes induced higher mRNA transfection efficiencies than non-crosslinked PBAP polyplexes, while non-crosslinked polyplexes showed similar mRNA transfection efficiencies to Lipo 2000.

The high mRNA delivery efficacy observed with the crosslinked CLPBAP polyplexes in multiple cell lines may be attributed to its crosslinked nature, which may keep the polyplex and mRNA—which is chemically less stable than some of the other genetic materials such as DNA—from disassembling and degrading before it reaches the cytosol. The enhanced stability exhibited by the crossliinked CLPBAP polyplex makes it potentially advantageous for mRNA delivery.

CRISPR-Cas9 Genome Editing Machinery Delivery Studies

Figure 14:
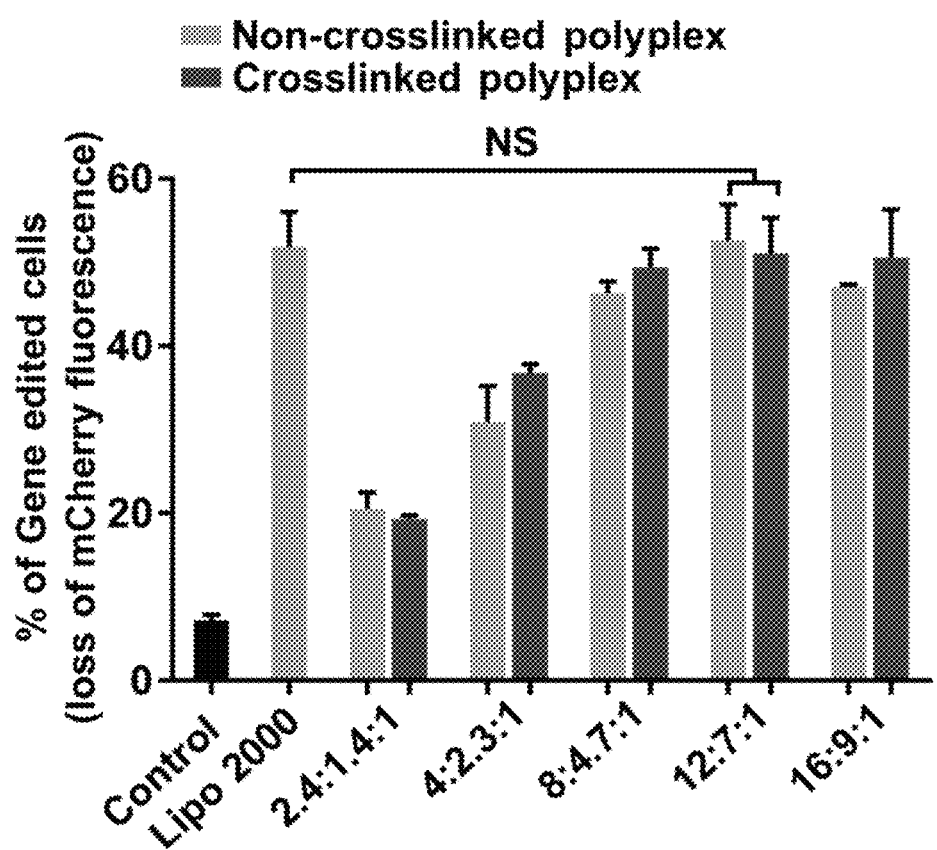
FIG. 14. Genome editing efficiency of non-crosslinked and crosslinked RNP polyplexes in mCherry-expressing HEK293 cells. The RNP polyplexes were prepared by varying the polymer-to-RNP weight ratios (i.e., PBAP:PEG-PBAP-PEG:RNP for non-crosslinked polyplexes, or CLPBAP:PEG-CLPBAP-PEG:RNP for crosslinked polyplexes). mCherry knock-out efficiency by the delivered RNP was detected by flow cytometry. NS: not significant. n=3.
Figure 15:
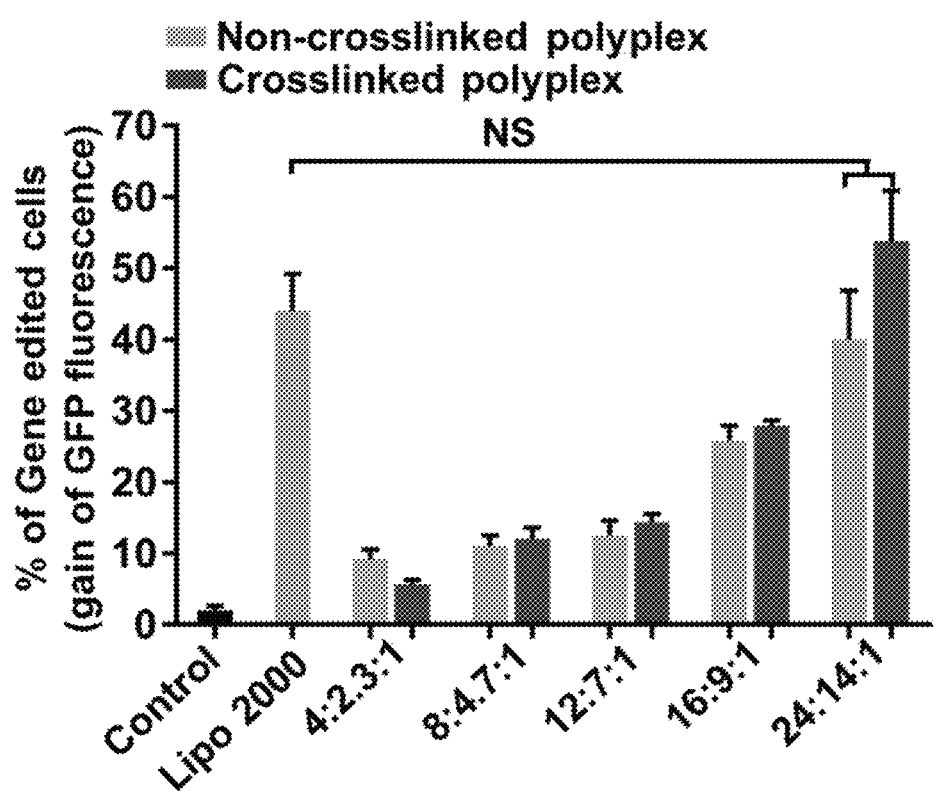
FIG. 15. Precise gene correction efficiency of the non-crosslinked and crosslinked S1mplex polyplexes in BFP-expressing HEK 293 cells. S1mplex polyplexes were prepared by varying the polymer-to-S1mplex weight ratios (i.e., PBAP:PEG-PBAP-PEG:RNP for non-crosslinked polyplexes, or CLPBAP:PEG-CLPBAP-PEG:RNP for crosslinked polyplexes). Precise gene correction efficiency of the BFP to the GFP from the S1mplex ssODN repair template was assayed by flow cytometry by gain of GFP fluorescence within cells. NS: not significant; n=3.
Figure 16A:
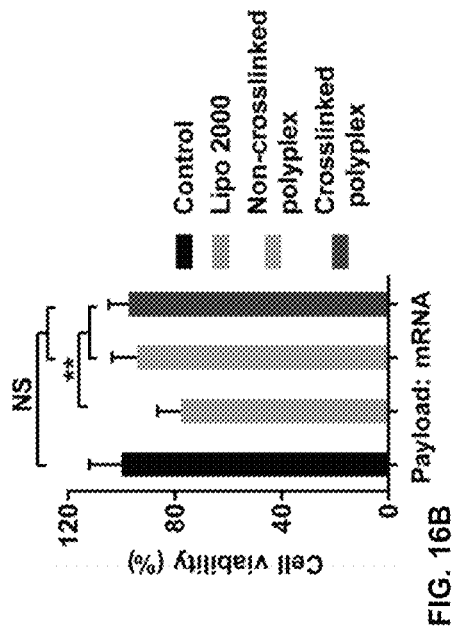
FIGS. 16A-16D. Cytoxocity of polyplexes in vitro. Cell viability study of the non-crosslinked and crosslinked complexes loaded with (FIG. 16A) DNA, (FIG. 16B) mRNA, (FIG. 16C) RNP, and (16D) S1mplex in HEK293 cells. Cytotoxicity was studied using the polymer/payload formulation yielding the highest transfection/genome editing efficiency. NS: not significant, **: p<0.01; n=5.
Figure 16B:
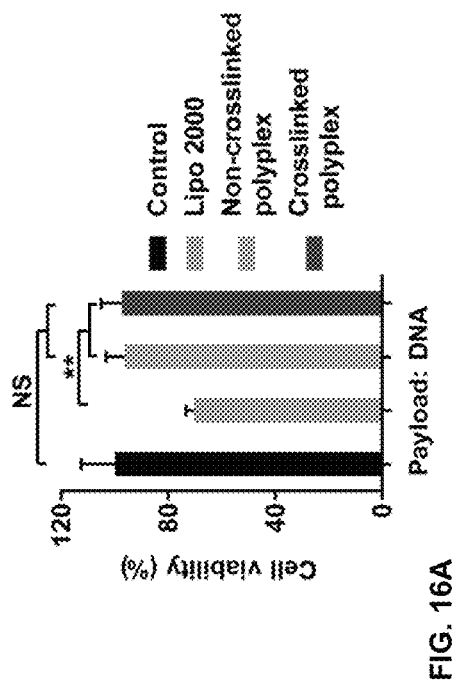
Figure 16C:
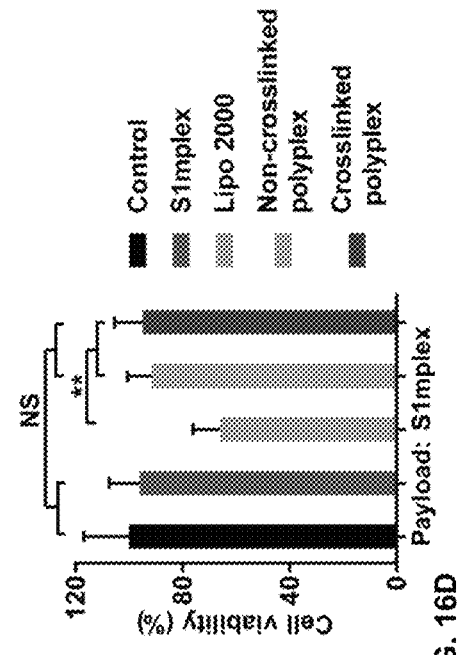
Figure 16D:
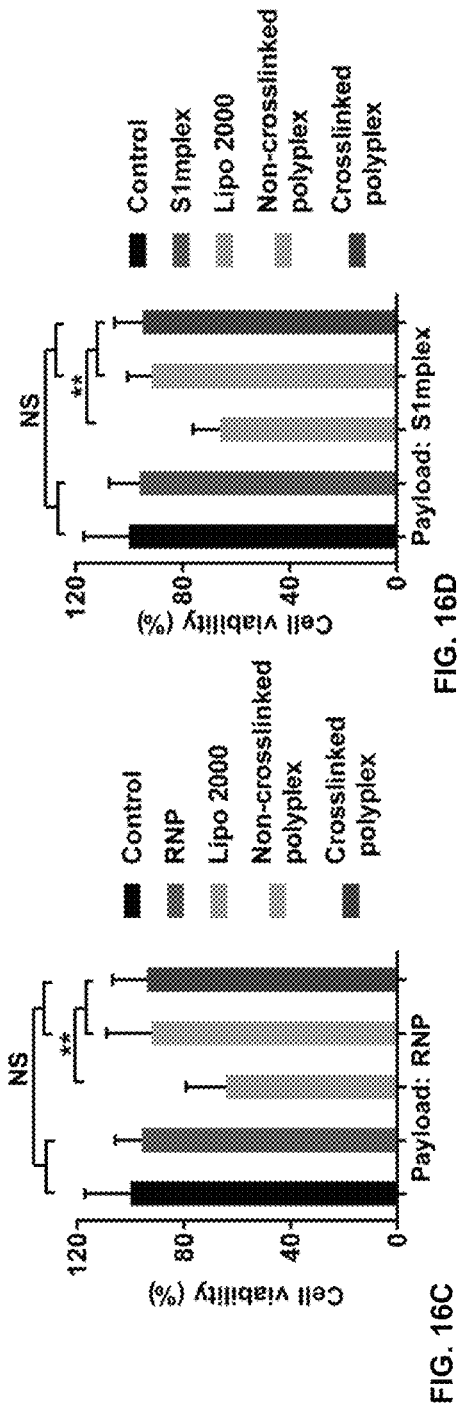

Compared to nucleic acids such as DNA and mRNA, CRISPR genome editing machineries such as Cas9/sgRNA RNP and Cas9/sgRNA-ssODN (e.g., S1mplex), have net negative surface charge and more sophisticated structures. To investigate whether non-crosslinked PBAP or crosslinked CLPBAP polyplexes can efficiently deliver RNP and to begin optimization of the polyplex formulation, Cas9/sgRNA RNP targeting the mCherry transgene in a transgenic HEK 293 cell line were used. To enhance the nuclear transportation, Cas9 protein with two NLS peptides (sNLS-Cas9-sNLS) was used to form the RNP complexes. Both non-crosslinked and crosslinked RNP polyplexes were prepared by varying the polymer and RNP weight ratios. As shown in FIG. 14, both non-crosslinked and crosslinked polyplexes exhibited the highest genome editing efficiencies for mCherry gene disruption at the PBAP:PEG-PBAP-PEG:RNP or CLPBAP:PEG-CLPBAP-PEG:RNP weight ratio of 12:7:1. Furthermore, both non-crosslinked and crosslinked polyplexes possessed similar targeted gene disruption efficiency to Lipo 2000, indicating its potential application for Cas9-based genome editing. These polyplexes also exhibited much lower cytotoxicity as described later and the crosslinked polyplexes also exhibited excellent stability.

In addition to gene disruption, gene editing applications could require precise gene correction using a repair nucleic acid template. The Cas9/sgRNA-ssODN complex (e.g., the S1mplex) is capable of gene disruption of the target gene, but is also capable of precise gene correction. The gene correction efficiency of both non-crosslinked and crosslinked S1mplex polyplexes were investigated using a BFP-expressing HEK 293 cell line. The S1mplex was designed to modify the BFP transgene to GFP through a three-nucleotide switch. The precise gene correction efficiency of the S1mplex polyplexes were monitored by flow cytometry by gating for GFP positive cells. As shown in FIG. 14, both non-crosslinked and crosslinked polyplexes induced a precise gene correction as indicated by significant GFP expression. Furthermore, at the PBAP:PEG-PBAP-PEG:RNP or CLPBAP:PEG-CLPBAP-PEG:RNP weight ratio of 24:14:1, the two types of polyplexes exhibited similar genome correction efficiency to Lipo 2000. These studies indicate that the non-crosslinked PBAP and crosslinked CLPBAP polyplexes are suitable for the delivery of not only nucleic acids, but also complex CRISPR genome editing machineries.

Cytotoxicity Studies.

The cytotoxicity of the polyplexes was studied by an MTT assay. The viability of cells was studied with the optimal polyplex formulation and the same payload concentration used in transfection/genome editing studies [i.e., for plasmid DNA and mRNA: 200 ng/well, at a PBAP (or CLPBAP):PEG-PBAP (or CLPBAP)-PEG:RNP weight ratio of 48:28:1; for RNP, 156 ng/well at a weight ratio of 12:7:1; for S1mplex: 235 ng/well at a weight ratio of 24:14:1]. As shown in FIGS. 16A-D, no significant cytotoxicity was associated with both non-crosslinked PBAP and crosslinked CLPBAP polyplexes treated groups, indicating good biocompatibility. In contrast, at the same payload dosage, Lipo 2000 induced significant cell death.

The cytotoxicity data, in combination with the transfection/genome editing efficiency studies, indicate that both types of polyplexes outperform the commercially available Lipo 2000 for delivery of nucleic acids and CRISPR-Cas9 genome editing agents. Furthermore, the crosslinked polyplexes also possess superior stability in the presence of polyanions such as BSA suggesting good in vivo stability due to its crosslinked structure. DNA, mRNA, Cas9 RNP, and Simplex are very different payloads both in terms of structure and functionality. Therefore, it is not surprising to see some of the reports suggesting that minor changes in the chemical structure of the cationic polymers can affect the transfection efficiency of DNA and mRNA differently. For example, the odd-even effects of the repeating aminoethylene units in the side chain of N-substituted polyaspartamides, had contradictory effects to DNA and mRNA transfection efficiencies owing to their different endosomal escape capabilities. Furthermore, studies also found that minor changes in the chemical structure of the cationic polymers can also dramatically affect the transfection efficiency of the same payload (e.g., DNA). We did not observe such sensitive changes in transfection efficiency with our nanoplatform, as it had broad versatility for several different payloads. This versatility is likely to facilitate the delivery of more CRISPR variant payloads, such as epigenomic editors, RNA editors and base editors. Further, other gene editing systems such as zinc finger nucleases and TAL-like effector nucleases maybe loaded into this nanoplatform.

One key advantage of the nanoplatform is the ease of formulation once the PBAP polymers have been synthesized. The PBAP polymers could be off-the-shelf reagents that can be mixed with many payloads within an hour and easily optimized for each particular payload and clinical application. Incorporation of targeting ligands onto the PBAP polymers would further add versatility and potential cell-targeting capability of the nanoplatform. Overall, we anticipate the nanoplatform to be easily customized by researchers without a synthetic chemistry expertise, such as engineers, biologists and clinicians, for potent gene editing in vitro and in vivo.

REFERENCES

[1] J. Carlson-Stevermer, et al., *Nature Communications* 2017, 8, 1711.
[2] S. M. Sarett, et al., *Journal of Controlled Release* 2001, 76, 169; Y. Lee, et al., *Angewandte Chemie* 2008, 120, 5241; M. Oba, et al., N. Nishiyama, *Biomaterials* 2011, 32, 652.
[3] R. E. Wang, et al., *Journal of Pharmaceutical and Biomedical Analysis* 2012, 63, 165.
[4] R. R. Arvizo, et al., *Nano letters* 2010, 10, 2543; E. Fröhlich, *International Journal of Nanomedicine* 2012, 7, 5577.

EQUIVALENTS

While certain embodiments have been illustrated and described, a person with ordinary skill in the art, after reading the foregoing specification, can effect changes, substitutions of equivalents and other types of alterations to the polyplexes of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A polyplex comprising:
   a payload selected from a protein and/or a polynucleic acid or protein/nucleic acid complex; and
   a plurality of copolymers comprising
   a first copolymer that is poly(N,N'-bis(acryloyl)cystamine-poly(aminoalkyl)) (PBAP),
   optionally a second copolymer that is poly($C_{2-3}$ akylene glycol)-PBAP-poly($C_{2-3}$ akylene glycol), and
   optionally a third copolymer that is TG-poly($C_{2-3}$ akylene glycol)-PBAP-poly($C_{2-3}$ akylene glycol)-TG wherein TG at each occurrence is independently a targeting ligand, a cell penetrating peptide, an imaging agent or a capping group, provided that a plurality of TG groups is a targeting ligand;
   wherein
   the payload is non-covalently complexed to one or more of the copolymers,
   one or more of the first, second, and/or third copolymers comprises an endosomal escape group having a pKa of about 4.5 to about 6.5, and optionally
   one or more of the first, second, and/or third copolymers comprises a host and a guest non-covalent crosslinker.

2. The polyplex of claim 1, wherein the payload has a net negative charge.

3. The polyplex of claim 1 wherein the payload is selected from the group consisting of pDNA, cDNA, ssODN, mRNA, siRNA, miRNA, shRNA, sgRNA, tRNA and ribozymes.

4. The polyplex of claim 1 wherein the payload is selected from the group consisting of Cas9 RNP, S1mplex, and other Cas9-based protein/nucleic acid complexes.

5. The polyplex of claim 1 wherein the first copolymer has the structure of Formula I:

wherein
$R^1$ and $R^2$ at each occurrence are independently selected from H, a $C_{2-5}$ alkyl amino group optionally protected by an amino protecting group, a $C_{2-5}$ alkyl amino group covalently linked to the endosomal escape group, a host-guest non-covalent crosslinker, or an imaging agent provided that at least one occurrence of $R^1$ and $R^2$ is a $C_{2-5}$ alkyl amino group covalently linked to the endosomal escape group in each subunit present p times;
$R^3$ and $R^4$ at each occurrence are independently selected from H or $C_{1-4}$ alkyl;
$R^5$ and $R^6$ are independently —$CH_2(CH_2)_{1-4}NHC(O)$—$CHR^4$=$CH_2$;
n at each occurrence is independently 1, 2, 3, or 4;
m at each occurrence is independently 1, 2, or 3;
p is an integer from 10 to 300 and
q and r at each occurrence are independently 1, 2, 3, or 4.

6. The polyplex of claim 5, wherein p is an integer from 10 to 35.

7. The polyplex of claim 1 wherein the second copolymer is present and has the structure of Formula II:

(II)

wherein
$R^1$ and $R^2$ at each occurrence are independently selected from a $C_{2-5}$ alkyl amino group optionally protected by an amino protecting group, a $C_{2-5}$ alkyl amino group covalently linked to the endosomal escape group or a host or guest non-covalent crosslinker;
$R^3$ and $R^4$ at each occurrence are independently selected from H or $C_{1-4}$ alkyl;
$R^7$ and $R^8$ are independently —[$CH_2CH_2O$]$_x$—$R^a$ or —[$CH_2CH(CH_3)O$]$_x$—$R^a$;
$R^a$ at each occurrence is H or a $C_{1-6}$ alkyl group;
n at each occurrence is independently 1, 2, 3, or 4;
m at each occurrence is independently 1, 2, or 3;
p' is an integer from 10 to 300;
q and r at each occurrence are independently 1, 2, 3, or 4; and
x at each occurrence is independently 2 to 500.

(I)

8. The polyplex of claim 7, wherein p' is an integer from 10 to 25.

9. The polyplex of claim 1 wherein the third copolymer is present and has the structure of Formula III:

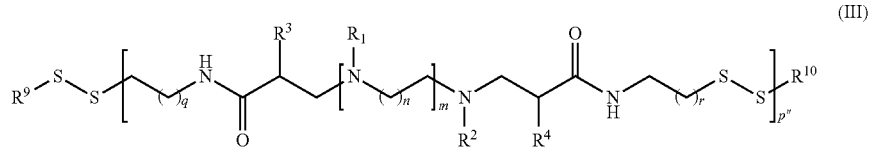

(III)

wherein
- $R^1$ and $R^2$ at each occurrence are independently selected from H, a $C_{2-5}$ alkyl amino group optionally protected by an amino protecting group, a $C_{2-5}$ alkyl amino group covalently linked to the endosomal escape group or a host or guest non-covalent crosslinker;
- $R^3$ and $R^4$ at each occurrence are independently selected from H or $C_{1-4}$ alkyl;
- $R^9$ and $R^{10}$ are independently $-[CH_2CH_2O]_x-R^b$ or $-[CH_2CH(CH_3)O]_x-R^b$;
- $R^b$ at each occurrence is H, a $C_{1-4}$ alkyl group, a $C_{2-4}$ alkyl group substituted with a functional group selected from an $NH_2$, COOH, maleimide, N-hydroxysuccinimide, isocyanate, azide, or alkyne group, a targeting ligand, cell penetrating peptide, or an imaging agent;
- n at each occurrence is independently 1, 2, 3, or 4;
- m at each occurrence is independently 1, 2, or 3;
- p" is an integer from 10 to 300;
- q and r at each occurrence are independently 1, 2, 3, or 4; and
- x at each occurrence is independently 2 to 500.

10. The polyplex of claim 9, wherein p" is an integer from 10 to 25.

11. The polyplex of claim 5 wherein $R^1$ and $R^2$ at each occurrence are independently selected from a $C_{2-5}$ alkyl amino group optionally protected by an amino protecting group, a $C_{2-3}$ alkyl amino group covalently linked to the endosomal escape group, or a $C_{2-5}$ alkyl amino group covalently linked to the host-guest crosslinker.

12. The polyplex of claim 5 wherein $R^3$ and $R^4$ at each occurrence are independently selected from H or methyl.

13. The polyplex of claim 5 wherein $R^5$ and $R^6$ are independently $-CH_2(CH_2)_{1-2}NHC(O)-CHR^4=CH_2$ and $R^4$ is H or methyl.

14. The polyplex of claim 6 wherein $R^7$ and $R^8$ are independently $-[CH_2CH_2O]^x-R^a$ and $R^a$ at each occurrence is H or methyl.

15. The polyplex of claim 7 wherein $R^9$ and $R^{10}$ are independently $-[CH_2CH_2O]_x-R^b$.

16. The polyplex of claim 5 wherein n is 1 or 2.

17. The polyplex of claim 5 wherein m is 1.

18. The polyplex of claim 5 wherein each of q and r is 1.

19. The polyplex of claim 5 wherein one or more occurrences of $R^1$ and $R^2$ are selected from a $C_{2-5}$ alkyl amino group covalently linked to the endosomal escape group and one or more occurrences of $R^1$ and $R^2$ are selected from a $C_{2-5}$ alkyl amino group covalently linked to a host-guest non-covalent crosslinker in each subunit present p times.

20. The polyplex of claim 19 wherein one or more occurrences of $R^1$ and $R^2$ are selected from a $C_{2-3}$ alkyl amino group covalently linked to the endosomal escape group and one or more occurrences of $R^1$ and $R^2$ are selected from a $C_{2-3}$ alkyl amino group covalently linked to a host-guest non-covalent crosslinker in each subunit present p times.

21. The polyplex of claim 5 wherein the host-guest non-covalent crosslinker is a β-cyclodextrin/adamantane pair.

22. The polyplex of claim 1 wherein the endosomal escape group is an imidazole group.

23. The polyplex of claim 22 wherein the imidazole group is covalently linked to the first, second, and/or third copolymer via an amide group.

24. The polyplex of claim 1 wherein the targeting ligand of the third copolymer is selected from the group consisting of cell penetrating peptides, aptamers, cofactors, carbohydrates, peptides, and proteins.

25. The polyplex of claim 1 wherein the imaging agent is selected from the group consisting of fluorescent dyes and radioisotope-chelants.

26. The polyplex of claim 1 wherein the weight ratio of first copolymer to second copolymer ranges from 1:1 to 5:1.

27. The polyplex of claim 1 wherein the weight ratio of first copolymer to the payload ranges from 2:1 to 100:1.

28. The polyplex of claim 1 wherein the weight ratio of second copolymer to the payload ranges from 1:1 to 20:1.

29. A method of delivering a payload to a targeted cell comprising exposing the targeted cell to the polyplex of claim 1.

30. The method of claim 29 comprising administering the polyplex to a subject in need thereof.

31. The method of claim 30 wherein the subject is a human.

32. The method of claim 29 wherein the payload is a Cas9 RNP.

* * * * *

UNITED STATES PATENT AND TRADEMARK OFFICE
CERTIFICATE OF CORRECTION

PATENT NO. : 11,351,263 B2  
APPLICATION NO. : 16/282174  
DATED : June 7, 2022  
INVENTOR(S) : Shaoqin Gong et al.

Page 1 of 1

It is certified that error appears in the above-identified patent and that said Letters Patent is hereby corrected as shown below:

In the Claims

Claim 14, Column 49, Line 45 should read:
independently $-[CH_2CH_2O]_x-R^a$ and $R^a$ at each occurrence Signed and Sealed this
Twentieth Day of December, 2022

Katherine Kelly Vidal
*Director of the United States Patent and Trademark Office*

```
                        SEQUENCE LISTING

<160> NUMBER OF SEQ ID NOS: 43

<210> SEQ ID NO 1
<211> LENGTH: 12
<212> TYPE: PRT
<213> ORGANISM: Human immunodeficiency virus

<400> SEQUENCE: 1

Gly Arg Lys Lys Arg Arg Gln Arg Arg Arg Pro Gln
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Leu Ala Leu Lys Leu Ala Leu Lys Ala Leu Lys Ala Ala Leu Lys
1               5                   10                  15

Leu Ala

<210> SEQ ID NO 3
<211> LENGTH: 15
<212> TYPE: PRT
<213> ORGANISM: Drosophila sp.

<400> SEQUENCE: 3
```

```
Arg Gln Ile Lys Trp Phe Gln Asn Arg Arg Met Lys Trp Lys Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gln Ile Arg Ile Trp Phe Gln Asn Arg Arg Met Arg Trp Arg Arg
1               5                   10                  15

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ser Ile Pro Pro Glu Val Lys Phe Asn Lys Pro Phe Val Tyr Leu
1               5                   10                  15
Ile

<210> SEQ ID NO 6
<211> LENGTH: 13
<212> TYPE: PRT
<213> ORGANISM: Rana temporaria

<400> SEQUENCE: 6

Phe Val Gln Trp Phe Ser Lys Phe Leu Gly Arg Ile Leu
1               5                   10

<210> SEQ ID NO 7
<211> LENGTH: 10
<212> TYPE: PRT
<213> ORGANISM: Maurus palmatus

<400> SEQUENCE: 7

Gly Asp Cys Leu Pro His Leu Lys Leu Cys
1               5                   10

<210> SEQ ID NO 8
<211> LENGTH: 18
<212> TYPE: PRT
<213> ORGANISM: Mus sp.

<400> SEQUENCE: 8

Leu Leu Ile Ile Leu Arg Arg Arg Ile Arg Lys Gln Ala His Ala His
1               5                   10                  15
Ser Lys

<210> SEQ ID NO 9
<211> LENGTH: 24
<212> TYPE: PRT
<213> ORGANISM: Homo sapiens

<400> SEQUENCE: 9

Leu Gly Thr Tyr Thr Gln Asp Phe Asn Lys Phe His Thr Phe Pro Gln
1               5                   10                  15
```

-continued

Thr Ala Ile Gly Val Gly Ala Pro
            20

<210> SEQ ID NO 10
<211> LENGTH: 30
<212> TYPE: PRT
<213> ORGANISM: Unknown
<220> FEATURE:
<223> OTHER INFORMATION: Description of Unknown:
      Neurturin sequence

<400> SEQUENCE: 10

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 11
<211> LENGTH: 18
<212> TYPE: PRT
<213> ORGANISM: Drosophila sp.

<400> SEQUENCE: 11

Arg Gln Ile Lys Ile Trp Phe Gln Asn Arg Arg Met Lys Trp Lys Lys
1               5                   10                  15

Gly Gly

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 13
<211> LENGTH: 11
<212> TYPE: PRT
<213> ORGANISM: Human immunodeficiency virus

<400> SEQUENCE: 13

Tyr Gly Arg Lys Lys Arg Arg Gln Arg Arg Arg
1               5                   10

<210> SEQ ID NO 14
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 14

Arg Gly Gly Arg Leu Ser Tyr Ser Arg Arg Arg Phe Ser Thr Ser Thr
1               5                   10                  15

Gly Arg

<210> SEQ ID NO 15

```
<211> LENGTH: 10
<212> TYPE: PRT
<213> ORGANISM: Unknown
<220> FEATURE:
<223> OTHER INFORMATION: Description of Unknown:
      SynB3 sequence

<400> SEQUENCE: 15

Arg Arg Leu Ser Tyr Ser Arg Arg Arg Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ile Arg Arg Arg Lys Lys Leu Arg Arg Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Gln Arg Arg Thr Ser Lys Leu Met Lys Arg
1               5                   10

<210> SEQ ID NO 18
<211> LENGTH: 15
<212> TYPE: PRT
<213> ORGANISM: Flock House virus

<400> SEQUENCE: 18

Arg Arg Arg Arg Asn Arg Thr Arg Arg Asn Arg Arg Arg Val Arg
1               5                   10                  15

<210> SEQ ID NO 19
<211> LENGTH: 19
<212> TYPE: PRT
<213> ORGANISM: Brome Mosaic virus

<400> SEQUENCE: 19

Lys Met Thr Arg Ala Gln Arg Arg Ala Ala Ala Arg Arg Asn Arg Trp
1               5                   10                  15

Thr Ala Arg

<210> SEQ ID NO 20
<211> LENGTH: 13
<212> TYPE: PRT
<213> ORGANISM: Human T-cell leukemia virus II

<400> SEQUENCE: 20

Thr Arg Arg Gln Arg Thr Arg Arg Ala Arg Arg Asn Arg
1               5                   10

<210> SEQ ID NO 21
<211> LENGTH: 13
<212> TYPE: PRT
```

```
<213> ORGANISM: Human immunodeficiency virus

<400> SEQUENCE: 21

Gly Arg Lys Lys Arg Arg Gln Arg Arg Arg Pro Pro Gln
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Arg Arg Arg Arg Arg Arg Arg Arg Arg Pro Pro Gln
1               5                   10

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 24
<211> LENGTH: 27
<212> TYPE: PRT
<213> ORGANISM: Homo sapiens

<400> SEQUENCE: 24

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 25
<211> LENGTH: 27
<212> TYPE: PRT
<213> ORGANISM: Unknown
<220> FEATURE:
<223> OTHER INFORMATION: Description of Unknown:
      FBP sequence

<400> SEQUENCE: 25

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

-continued

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 30

Arg Arg Arg Arg Arg Arg Arg Arg Arg Arg Arg Arg Arg Arg Arg Arg
1               5                   10                  15

Arg
```

-continued

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 31

Lys Lys Lys Lys Lys Lys Lys Lys Lys Lys Lys Lys Lys Lys Lys Lys
1               5                   10                  15

Lys

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminocaproic acid
<220> FEATURE:
<221> NAME/KEY: MOD_RES
<222> LOCATION: (4)..(4)
<223> OTHER INFORMATION: Aminocaproic acid
<220> FEATURE:
<221> NAME/KEY: MOD_RES
<222> LOCATION: (6)..(6)
<223> OTHER INFORMATION: Aminocaproic acid
<220> FEATURE:
<221> NAME/KEY: MOD_RES
<222> LOCATION: (8)..(8)
<223> OTHER INFORMATION: Aminocaproic acid
<220> FEATURE:
<221> NAME/KEY: MOD_RES
<222> LOCATION: (10)..(10)
<223> OTHER INFORMATION: Aminocaproic acid
<220> FEATURE:
<221> NAME/KEY: MOD_RES
<222> LOCATION: (12)..(12)
<223> OTHER INFORMATION: Aminocaproic acid

<400> SEQUENCE: 32

Arg Xaa Arg Xaa Arg Xaa Arg Xaa Arg Xaa Arg Xaa Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (4)..(4)
<223> OTHER INFORMATION: Aminobutyric acid
<220> FEATURE:
<221> NAME/KEY: MOD_RES
<222> LOCATION: (6)..(6)
<223> OTHER INFORMATION: Aminobutyric acid
<220> FEATURE:
<221> NAME/KEY: MOD_RES
```

```
<222> LOCATION: (8)..(8)
<223> OTHER INFORMATION: Aminobutyric acid
<220> FEATURE:
<221> NAME/KEY: MOD_RES
<222> LOCATION: (10)..(10)
<223> OTHER INFORMATION: Aminobutyric acid
<220> FEATURE:
<221> NAME/KEY: MOD_RES
<222> LOCATION: (12)..(12)
<223> OTHER INFORMATION: Aminobutyric acid

<400> SEQUENCE: 33

Arg Xaa Arg Xaa Arg Xaa Arg Xaa Arg Xaa Arg Xaa Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gly Arg Gly Arg Gly Arg Gly Arg Gly Arg Gly Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Met Arg Met Arg Met Arg Met Arg Met Arg Met Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Thr Arg Thr Arg Thr Arg Thr Arg Thr Arg Thr Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Arg Ser Arg Ser Arg Ser Arg Ser Arg Ser Arg
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 38

Arg Arg Arg Arg Arg Arg Arg Arg Arg Arg
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Arg Ala Arg Ala Arg Ala Arg Ala Arg Ala Arg
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Arg Arg Arg Arg Arg Arg
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Lys Lys Lys Lys Arg Lys Val
1               5

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggagccgtac atgaactgag                                           20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gctgaagcac tgcacgccat                                           20
```